United States Patent
Borsic

(10) Patent No.: US 11,908,584 B2
(45) Date of Patent: Feb. 20, 2024

(54) METHODS AND SYSTEMS FOR MODELING A NECROTIZED TISSUE VOLUME IN AN ABLATION PROCEDURE

(71) Applicant: NE Scientific, LLC, Boston, MA (US)

(72) Inventor: Andrea Borsic, Turin (IT)

(73) Assignee: NE Scientific, LLC, Boston, MA (US)

( * ) Notice: Subject to any disclaimer, the term of this patent is extended or adjusted under 35 U.S.C. 154(b) by 1138 days.

(21) Appl. No.: 16/541,621

(22) Filed: Aug. 15, 2019

(65) Prior Publication Data

US 2019/0371474 A1 Dec. 5, 2019

Related U.S. Application Data

(63) Continuation-in-part of application No. 15/595,737, filed on May 15, 2017, now abandoned.

(51) Int. Cl.
| | | |
|---|---|---|
| *G16H 50/50* | (2018.01) | |
| *G16H 20/40* | (2018.01) | |
| *G16H 30/40* | (2018.01) | |
| *A61B 34/10* | (2016.01) | |
| *A61B 18/00* | (2006.01) | |

(52) U.S. Cl.
CPC ............ *G16H 50/50* (2018.01); *A61B 34/10* (2016.02); *G16H 20/40* (2018.01); *G16H 30/40* (2018.01); *A61B 2018/00577* (2013.01)

(58) Field of Classification Search
CPC ............. G16H 50/50; A61B 18/1477; A61B 2034/107; A61B 2034/105; A61B 2018/00577; A61B 2018/00797; A61B 2005/0084; A61B 2034/2051; A61B 2090/0378; A61B 34/10
See application file for complete search history.

(56) References Cited

U.S. PATENT DOCUMENTS 6,395,000 B1   5/2002 Mitchell et al.
7,467,075 B2  12/2008 Humphries et al.
(Continued)

OTHER PUBLICATIONS

Wang et al., "Expanding the Bioheat Equation to Include Tissue Interal Water Evaporation During Heating", Aug. 2007, IEEE Transactions on Biomedical Engineering, vol. 54, No. 8, 1382-1388 (Year: 2007).*

(Continued)

*Primary Examiner* — Ronald Hupczey, Jr.
(74) *Attorney, Agent, or Firm* — Pandiscio & Pandiscio

(57) ABSTRACT

A system for modeling a necrotized tissue volume in an ablation procedure includes a radiology workstation designed and configured to provide a computer model of a volume of human tissue based on corporeal image data, simulate an ablation site in the computer model, detect, in the computer model, at least a preferential pathway for heated vapor produced due to ablation of the tissue, wherein the at least a preferential pathway intersects the ablation site, determine a proportion of vapor escaping to the at least a preferential pathway during an ablation procedure, determiner a heat distribution at the ablation site as a function of the distribution of vapor, and generate a simulation of a necrotized tissue volume in the volume of tissue, wherein the simulation of the necrotized tissue volume represents a volume of tissue necrotized by heat during an ablation procedure performed at the ablation site.

20 Claims, 13 Drawing Sheets

(56) References Cited

U.S. PATENT DOCUMENTS

| | | |
|---|---|---|
| 8,600,719 B2 | 12/2013 | Altrogge et al. |
| 2004/0122323 A1 | 6/2004 | Vortman et al. |
| 2005/0209661 A1 | 9/2005 | Kassayan |
| 2006/0155195 A1 | 7/2006 | Maier et al. |
| 2007/0118101 A1 | 5/2007 | Mahesh et al. |
| 2007/0129626 A1 | 6/2007 | Mahesh et al. |
| 2009/0221898 A1 | 9/2009 | Hillis et al. |
| 2009/0221999 A1* | 9/2009 | Shahidi .................. A61B 34/10 128/898 |
| 2011/0191082 A1 | 8/2011 | Blezek et al. |
| 2013/0035921 A1 | 2/2013 | Rodriguez-Ponce et al. |
| 2015/0119870 A1 | 4/2015 | Rudie |
| 2017/0086923 A1 | 3/2017 | Rink et al. |
| 2017/0224402 A1 | 8/2017 | Borsic |
| 2018/0325424 A1 | 11/2018 | Borsic |
| 2019/0371474 A1 | 12/2019 | Borsic |

OTHER PUBLICATIONS

PCT/US2020/039390, International Search Report, dated Sep. 24, 2020.

Yang, D. et al., Expanding the Bioheat Equation to Include Tissue Internal Water Evaporation During Heating, IEEE Transactions on Biomedical Engineering, Aug. 2007, vol. 54, No. 8, pp. 1382-1388.

\* cited by examiner

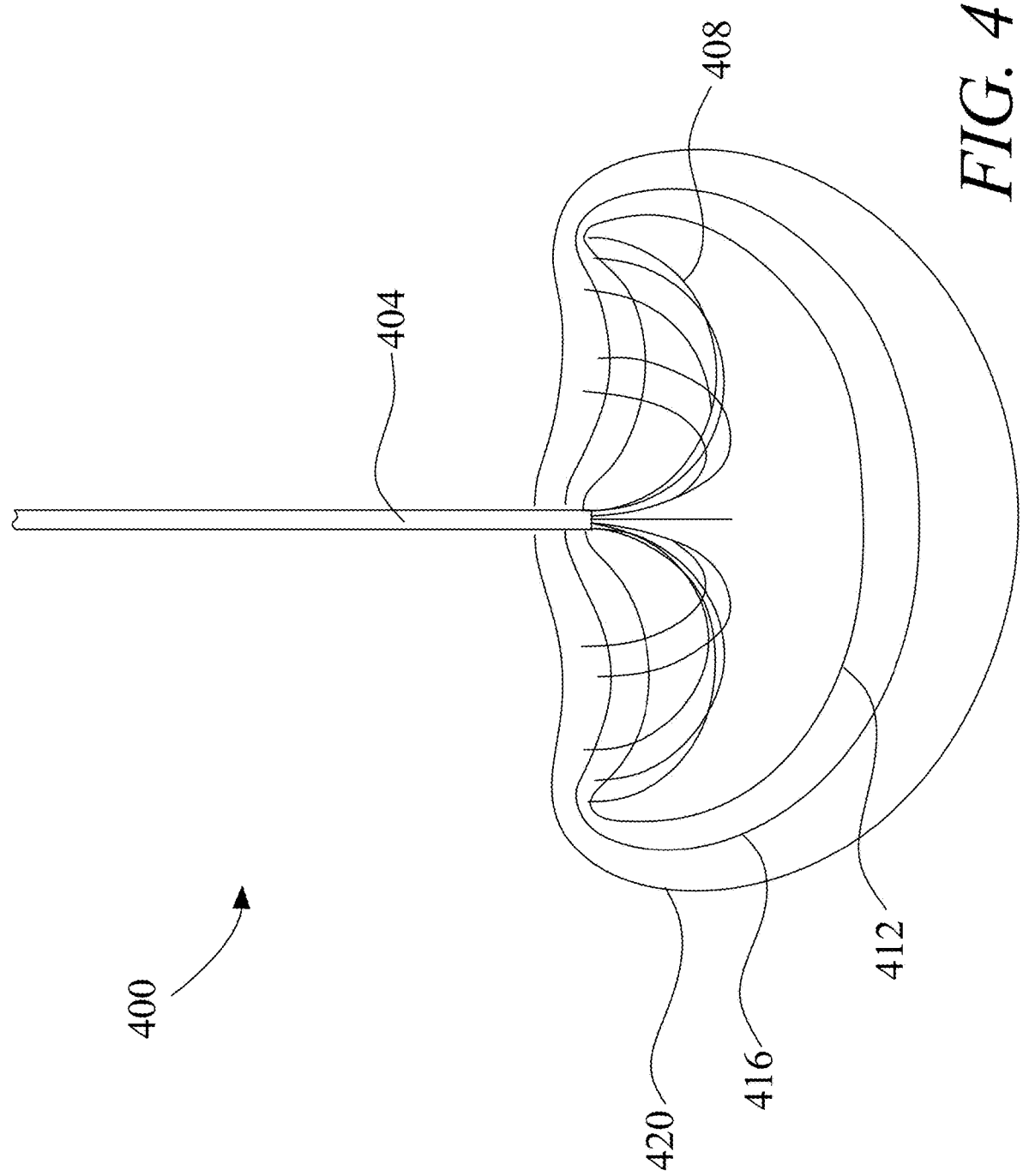

METHODS AND SYSTEMS FOR MODELING A NECROTIZED TISSUE VOLUME IN AN ABLATION PROCEDURE

CROSS-REFERENCE TO RELATED APPLICATIONS

This application is a continuation-in-part of Non-provisional Application Ser. No. 15/595,737 filed on May 15, 2017 and entitled "A METHOD FOR ESTIMATING THERMAL ABLATION VOLUME AND GEOMETRY," the entirety of which is incorporated herein by reference.

STATEMENT REGARDING FEDERALLY SPONSORED RESEARCH OR DEVELOPMENT

This invention was made with government support under R43 CA189515 awarded by the National Institutes of Health. The government has certain rights in the invention.

FIELD OF THE INVENTION

The present invention generally relates to the field of surgical planning and guidance. In particular, the present invention is directed to modeling a necrotized tissue volume in an ablation procedure.

BACKGROUND

Percutaneous thermal ablation is a procedure whereby pathological tissue is necrotized using high temperatures generated by a probe or needle inserted into the body. During a percutaneous ablation the vapor that forms is not able to leave the body. Existing evaporation models do not adequately account for the behavior of this vapor, leading to inaccurate predictions of the volume of necrotized tissue. This can lead to procedures that fail to remove the target tissue or damage healthy tissue to an unacceptable extent.

SUMMARY OF THE DISCLOSURE

In an aspect, a method of modeling a necrotized tissue volume in an ablation procedure includes providing, at a radiology workstation, a computer model of a volume of human tissue. The method includes simulating, by the RW, an ablation site in the computer model. The method includes detecting, by the RW and in the computer model, at least a preferential pathway for heated vapor produced due to ablation of the tissue, wherein the at least a preferential pathway intersects the ablation site. The method includes determining, by the RW, a proportion of vapor escaping to the at least a preferential pathway during an ablation procedure. The method includes determining, by the imaging device, a heat distribution at the ablation site as a function of the distribution of vapor. The method includes generating, by the imaging device, a simulation of a necrotized tissue volume in the volume of tissue, wherein the simulation of the necrotized tissue volume represents a volume of tissue necrotized by heat during an ablation procedure performed at the ablation site.

In another aspect, a system for modeling a necrotized tissue volume in an ablation procedure includes a radiology workstation, wherein the radiology workstation is designed and configured to provide a computer model of a volume of human tissue, simulate an ablation site in the computer model, detect, in the computer model, at least a preferential pathway for heated vapor produced due to ablation of the tissue, wherein the at least a preferential pathway intersects the ablation site, determine a proportion of vapor escaping to the at least a preferential pathway during an ablation procedure, determine a heat distribution at the ablation site as a function of the distribution of vapor, and generate a simulation of a necrotized tissue volume in the volume of tissue, wherein the simulation of the necrotized tissue volume represents a volume of tissue necrotized by heat during an ablation procedure performed at the ablation site.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 4 a schematic diagram illustrating exemplary embodiments of temperature isolines about an ablative probe;

Figure 1:
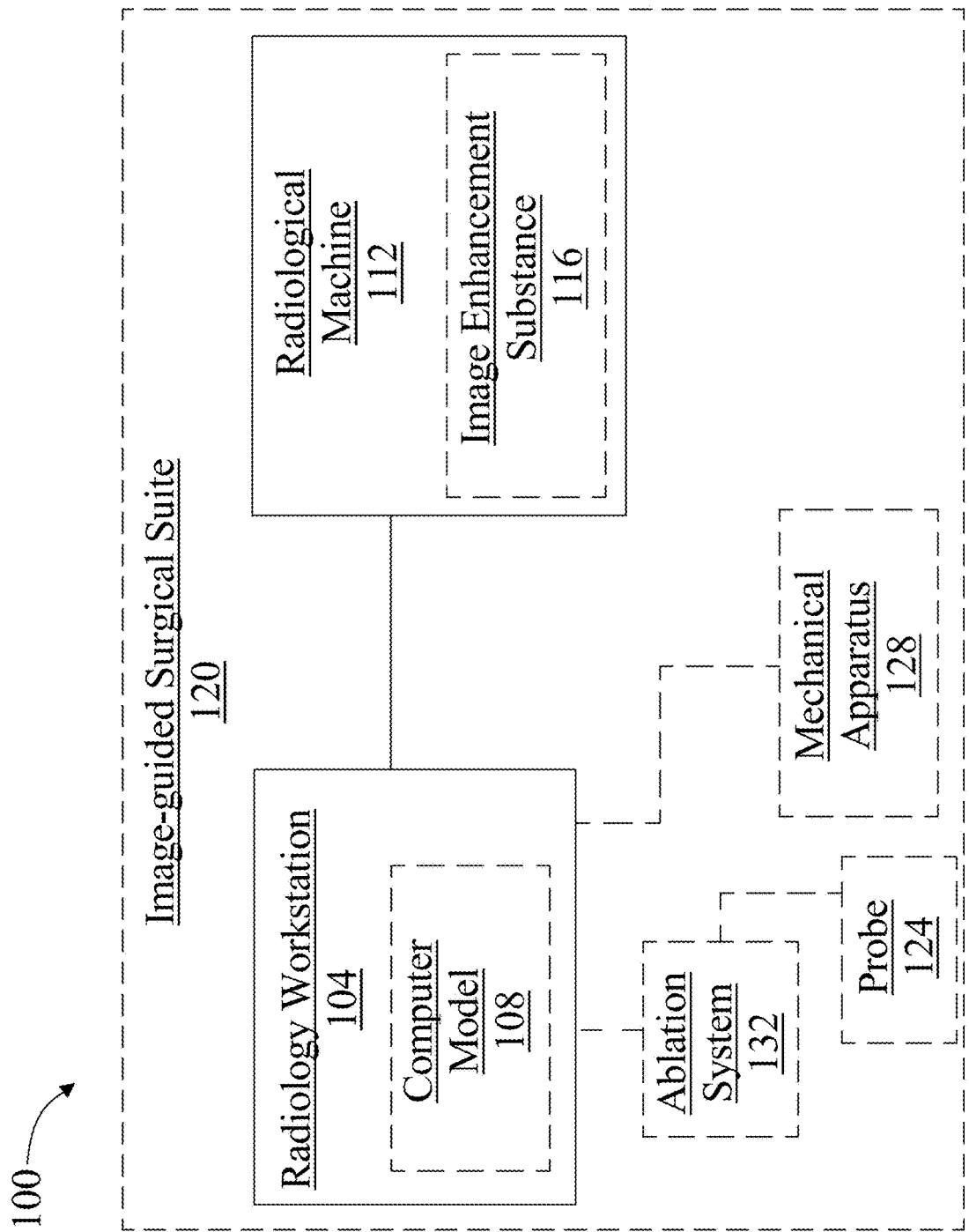
FIG. 1 is a block diagram illustrating an exemplary embodiment of a system for modeling a necrotized tissue volume in an ablation procedure.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Methods and systems as disclosed herein generate predictive models of ablated tissue by detecting preferential paths for vapor to travel through, modeling the effect of such vapor movement on tissue temperatures during ablation, and determining volumes of necrotized tissue as a result of the modeled temperature ranges. In embodiments, methods and systems as disclosed herein enable generation of visualizations that allow a physician to study which tissues would be treated by a particular ablation device, energy setting, and position/orientation of the device inside the body. A physician may be able to use such visualizations to plan an intervention, for example, by determining the single or multiple optimal positions/orientations of the ablation device inside the body, and levels of applied energy to use, which may result in the complete treatment of the target tissues; complications may be minimized by accurate planning as well. Intraoperative guidance and/or planning according to systems and methods as disclosed herein may be performed in advance, including days in advance, of the procedure in question; alternatively or additionally, intraoperative guidance and/or planning may be performed during a medical procedure such as a percutaneous ablation procedure or a procedure involving percutaneous ablation.

Systems and methods as described herein may be deployed within the context of systems, processes, and procedures for thermal ablation of human or animal tissue. Thermal ablation is a process whereby abnormal or pathological tissues are selectively heated until cell death occurs, causing the abnormal or pathological tissues to die. Thermal ablation technologies may use to treat tissues for therapeutic purposes. An example of application may include treatment of cancer, where thermal ablation is used to necrotize malignant tissues in order to cure or manage the disease.

As a non-limiting example a technique for thermal ablation may fall into one of two frequently used categories: Radio Frequency Ablation (RFA) and Microwave Ablation (MWA). RFA is based on the application of Radio Frequency (RF) energy to the tissues by means of one or multiple contacting electrodes. MWA is based on the application of Micro Wave (MW) energy to the tissues by means of a contacting antenna. Both technologies cause a local increase in the temperature of tissues which ultimately causes the necrosis of a certain volume of tissues (treatment of tissues). If the volume of treated tissues encompasses all the tissues which are target of the procedure, the treatment is adequate. A single procedure may require multiple overlapping ablations to treat the whole volume of target tissues. Each of RFA and MWA can be applied in a minimally invasive fashion. Both RFA and MWA are, for example, used in percutaneous treatment of liver cancer, where a needle-shaped RFA electrode, or MWA antenna, are inserted, through the skin, into the volume of the tumor and used to treat the target tissues.

As a non-limiting example, during RFA, an electrode with an un-insulated tip may be inserted into a tumor or lesion to be ablated under guidance of medical imaging, such as ultrasound, computed tomography (CT) or magnetic resonance imaging (MM). Once the electrode is placed, a radiofrequency current may be applied to the tip creating tissue heating and cell death. In order to destroy tumors that are larger than the volume around the needle tip that is heated and destroyed in a single ablation, the needle tip may be repeatedly repositioned to ablate different parts of the tumor, partly overlapping with one another. This process may be repeated until the entire tumor is "covered" by the plurality of ablations, also referred to as the "composite ablation." As during a percutaneous ablation the vapor that forms is not able to leave the body, existing evaporation models have assumed that the vapor which forms at the hottest points of the ablation site will diffuse in the porous matrix of tissues and condense at locations where the temperature of tissues is inferior to the evaporation temperature of water. In these models no vapor is therefore assumed to leave the body. Existing evaporation/condensation model therefore assume that evaporation occurs in a certain region of tissues (hotter) and that condensation occurs at other regions (colder). In regions where evaporation occurs, heat is absorbed from tissues by the evaporating water, in regions when condensation occurs heat is delivered to tissues by the condensing vapor. Existing methods have assumed that such vapor diffuses uniformly through adjacent tissues, failing to account for preferential pathways the vapor may follow, as described in further detail below; existing models also lack mechanisms whereby such preferential paths may be detected and used to predict ablation volumes more accurately.

Referring now to FIG. 1, an exemplary embodiment of a system 100 for modeling a necrotized tissue volume in an ablation procedure is illustrated. System 100 includes a radiology workstation 104. Radiology workstation 104 may include any computing device as described in this disclosure, including without limitation a microcontroller, microprocessor, digital signal processor (DSP) and/or system on a chip (SoC), or a Graphic Processing Unit (GPU) as described in this disclosure. Radiology workstation 104 may be housed with, may be incorporated in, or may incorporate one or more sensors of at least a sensor. Computing device may include, be included in, and/or communicate with a mobile device such as a mobile telephone or smartphone. Radiology workstation 104 may include a single computing device operating independently, or may include two or more computing device operating in concert, in parallel, sequentially or the like; two or more computing devices may be included together in a single computing device or in two or more computing devices. Radiology workstation 104 with one or more additional devices as described below in further detail via a network interface device. Network interface device may be utilized for connecting a radiology workstation 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Radiology workstation 104 may include but is not limited to, for example, a radiology workstation 104 or cluster of computing devices in a first location and a second computing device or cluster of computing devices in a second location. Radiology workstation 104 may include one or more computing devices dedicated to data storage, security, distribution of traffic for load balancing, and the like. Radiology workstation 104 may distribute one or more computing tasks as described below across a plurality of computing devices of computing device, which may operate in parallel, in series, redundantly, or in any other manner used for distribution of tasks or memory between computing devices. Radiology workstation 104 may be implemented using a "shared nothing" architecture in which data is cached at the worker, in an embodiment, this may enable scalability of system 100 and/or computing device.

Continuing to refer to FIG. 1, radiology workstation 104 may provide, store, receive, manipulate, or otherwise work with a computer model 108 of human or animal tissue. Computer model 108 may be used in conjunction with methods and/or method steps as described in further detail below. Computer model 108 may be provided and/or manipulated as described in further detail below.

Still referring to FIG. 1, in an embodiment, radiology workstation 104 may communicate with at least a radiological machine 112. At least a radiological machine 112 may include, without limitation, a device and/or suite of devices configured to capture and/or manipulate imaging data depicting human tissue; human tissue may be living tissue, including without limitation organ or other corporeal tissue of a prospective subject for an ablation procedure as described in this disclosure. Imaging data may include data describing and/or depicting tissue to be ablated, which may include abnormal and/or pathological tissue, such as tissue containing one or more malignant or benign tumors, lesions, cysts, scar tissue, or the like. Imaging data may include imaging data describing abnormal and/or pathological tissue itself; for instance, image data may describe and/or depict a tumor, lesion, cyst, or the like.

With continued reference to FIG. 1, imaging data may be captured using any technology, device, and/or system for capture of radiological imaging data in two-dimensional or three-dimensional form, or any combination thereof. As a non-limiting example, imaging data may be captured using computed tomography (CT). As a further non-limiting example, imaging data may be captured using X-ray and/or fluoroscopy. As an additional non-limiting example imaging data may be captured using magnetic resonance imaging (MRI). As a further non-limiting example, medical imaging data may be captured using a nuclear medicine scanning technique, such as a technique whereby a radiation, particle, or antiparticle-emitting substance is preferentially absorbed by abnormal and/or pathological tissue, and an image is formed by directly or indirectly capturing output generated by the emitting substance; non-limiting examples include positron-emission tomography (PET) scans. Medical imaging data may, in another non-limiting example, be acquired using photo-acoustic imagery. In an embodiment, and as a non-limiting example, imaging data may be captured using ultrasound technology. Imaging data may, as a further non-limiting example, be captured using optical scanning techniques. Radiological machine 112 may include, without limitation, a CT scanner, a C-arm image-acquisition device, an MRI scanner, or an US scanner; persons skilled in the art will be aware, upon reviewing the entirety of this disclosure, of various elements of radiological and/or medical imaging equipment that may be used to capture images. In an embodiment, two or more scanning methodologies and/or technologies may be combined to capture imaging data; for instance, MM may be combined with CT scanning initially or at different stages in an imaging process and/or procedure. As a further non-limiting example, CT and PET scanning may be combined to generate an image using imaging data captured from tissue. Persons skilled in the art, upon reviewing the entirety of this disclosure, will be aware of various ways in which scanning technology may be used and/or combined to capture imaging data as described in this disclosure.

Still referring to FIG. 1, in an embodiment, capture of imaging data is performed at least in part by introduction of one or more chemical substances having the property of enhancing the accuracy, contrast, effective resolution, and/or signal to noise ratio of resulting images and/or models of tissue. Such chemical substances, collectively referred to in this disclosure as "image enhancement substances," include without limitation contrast agents such as iodine, barium, gadolinium, or the like, radiopharmaceutical agents that emit particles and/or radiation directly or indirectly, including without limitation agents used in nuclear medicine imaging techniques as described above, fluorescent agents, or the like. Chemical substances may include one or more elements of high-contrast media in liquid, gas, or powder form. Persons skilled in the art, upon reviewing the entirety of this disclosure, will be aware of various forms of chemical substances that may be introduced to tissues to generate, improve, and/or calibrate images captured from the tissues. Chemical substances may be introduced by any suitable means, including without limitation ingestion in liquid or solid form, insertion into one or more orifices such as via enema and/or suppository, injection into tissue, veins, arteries, lymph ducts, and/or interstitial spaces, or insertion using an ablative probe and/or device as described below in further detail. Chemical substances may be paired with, incorporated in, or attached to one or more additional substances or structures aiding in selective absorption by or adhesion to one or more tissues or other anatomical structures of interest; for instance, chemical substances may be paired with, incorporated in, and/or attached to one or more monoclonal antibodies that selectively attach to cellular tissue having particular properties, including without limitation cancerous and/or precancerous tissue, tissue made up of a particular category of specialized cells, or the like.

With continued reference to FIG. 1, capture of imaging data may include capture and/or generation of a three-dimensional image of tissue. Three-dimensional image may be created, without limitation using a combination of a plurality of two-dimensional "slices" captured using imaging technology and/or processes as described above; as a non-limiting example, two-dimensional MRI, CT, or other images of a volume of tissue, such as without limitation an organ or body part, may be combined to generate a three-dimensional image, for instance by capturing a series of two-dimensional images separated by a given resolution space in succession. As a further non-limiting example, a three-dimensional image may be generated by capturing data in the form of a series or plurality of "pixels" and/or "voxels" that are combined to generate a three-dimensional image.

Still referring to FIG. 1, system 100 may communicate with and/or include an image-guided surgical suite 120. An "image-guided surgical suite" as used herein is a set of devices used to perform image-guided surgery. Such devices may include, without limitation, displays, mechanical devices, and/or imaging tools that guide or perform surgical actions including placement of probes for ablation procedures. Image-guided surgical suite 120 may generate intraoperative guidance visualizations indicating to a physician or other medical professional a current and/or target location of a probe 124, implant, scope, or other surgical instrument or item of equipment within a volume of tissue. For instance, and without limitation, image-guided surgical suite 120 may provide an initial image to a medical professional performing an ablation procedure, the initial image indicating at least an ablation site; indication of at least an ablation site may include indication of one or more areas or locations of abnormal or pathological tissue to be targeted using a probe 124. Initial image may include a target marker, which may include an added indicator marking an ablation site, such as without limitation an "X" or equivalent marking at a depiction of an ablation site, a circle around the depiction of the ablation site, or the like. Initial image may include a virtual and/or simulated image of a probe 124 as inserted into tissue at the ablation site, which may include depiction of a position and/or orientation of the probe 124. Initial image may include a plurality markings and/or virtual and/or simulated images of probes as described above as indicating a plurality of ablation sites; alternatively a plurality of initial images may be generated and/or displayed to indicate a plurality of ablation sites. Initial image and/or plurality of initial images may illustrate and/or depict a boundary surface and/or boundary line within which tissue has been necrotized, including during or involving a previous iteration of an embodiment of a method as described in this disclosure, and/or within which tissue is intended to be necrotized in a planned procedure, including without limitation a procedure as guided by processes as described herein.

Continuing to refer to FIG. 1, image-guided surgical suite 120 may provide repeated and/or updated images during probe 124 insertion and/or ablation; for instance image-guided surgical suite 120 may repeatedly capture and display images, using any imaging technology as described above, of patient tissue and/probe 124 during probe 124 insertion and/or ablation. Such repeated images may include a continuously updating display such as a video display showing insertion and/or ablation in real time, for instance to indicate to a medical professional a current position and/or orientation of a probe 124 as insertion and/or ablation is taking place, enabling the medical professional to correct a direction and/or angle of insertion and/or to plan a further insertion step; additional images such as elements suitable for use in an initial image as described above may be combined with and/or superimposed on images so displayed, for instance to depict for a medical professional both a target ablation site into which the probe 124 is to be inserted and a current position of the probe 124 during insertion. Imaging and/or modeling systems, methods and technologies, for instance as described herein, may support physicians in evaluating which tissues are to be treated, have been treated, or have not been treated by a particular ablation directly in the operating room, offering a "see-and-treat" functionality. Non-limiting examples of image-guided surgical suite 120s may include, without limitation, surgical instrument tracking technologies, including electromagnetic systems such the NDI Aurora system and/or optic systems such as the Medtronic StealthStation; persons skilled in the art, upon reviewing the entirety of this disclosure, will be aware of various additional or alternative image-guided surgical suite 120s and/or elements thereof, which may be employed consistently with this disclosure.

Still referring to FIG. 1, image-guided surgical suite 120 may include a mechanical apparatus 128, such as without limitation a robotic arm, which may be controlled using manual controls or robotically operated by a computing device in image-guided surgery suite. Mechanical apparatus 128 may alternatively or additionally include one or more mechanical components that constrain or guide manual actions and/or one or more patient body parts to ensure accurate and/or safe insertion of tools such as probes for ablation.

Continuing to refer to FIG. 1, system 100 may, in a non-limiting embodiment, include an ablation system 132. An "ablation system," as defined in this disclosure, is a device that provides energy to a probe 124. Ablation system 132 may control and/or regulate supply of energy to a probe, using any suitable energy regulator; where energy supply is electrical and/or may be regulated by electrical parameters such as voltage, current, resistance, or the like, ablation system 132 may regulate electrical voltage, current, and/or energy level and/or output to probe using any analog and/or voltage regulator and/or control device. For instance, and without limitation, radiology workstation 104 and/or other component of system may command and/or drive ablation system 132 to commence, cease, and/or vary energy output to a prove 124 according to any process as described below for estimation and/or determination of volumes of ablated and/or necrotized tissue, determining appropriate power levels, ablation locations, and/or duration of power supply at any power level, or the like. Ablation system 132 may alternatively or additionally be controlled by a user by way of one or more user controls, which may include any manual or other input devices as described in this disclosure, such as without limitation buttons, knobs, keys, a touch pad, a touch screen, a mouse, or the like, where a person operating ablation system 132 and/or system 100, such as without limitation a physician, may set a level of power applied, a duration of an ablation, and/or start and stop the ablation. Ablation system 132 may include, a computing device (not shown), which may include any device suitable for use as radiology workstation 104 as described above, and/or any other computing device as described in this description; ablation system 132 may be configured and/or programmed to perform any process step, process, repetitions, and/or iterations thereof that may be performed by radiology workstation 104 as described in this disclosure.

With continued reference to FIG. 1, radiology workstation 104 may be configured to perform any embodiment of any method and/or of any method steps as described and/or alluded to in this disclosure, in any degree of repetition, and in any order. For instance, and without limitation, radiology workstation 104 may be designed and/or configured to provide a computer model 108 of a volume of biological tissue, simulate an ablation site in the computer model 108, detect, in the computer model 108, at least a preferential pathway for heated vapor produced due to ablation of the tissue, wherein the at least a preferential pathway intersects the ablation site, determine a proportion of vapor escaping to the at least a preferential pathway during an ablation procedure, determiner a heat distribution at the ablation site as a function of the distribution of vapor, and generate a simulation of a necrotized tissue volume in the volume of tissue, wherein the simulation of the necrotized tissue volume represents a volume of tissue necrotized by heat during an ablation procedure performed at the ablation site, for instance and without limitation as described in further detail below.

Figure 2:
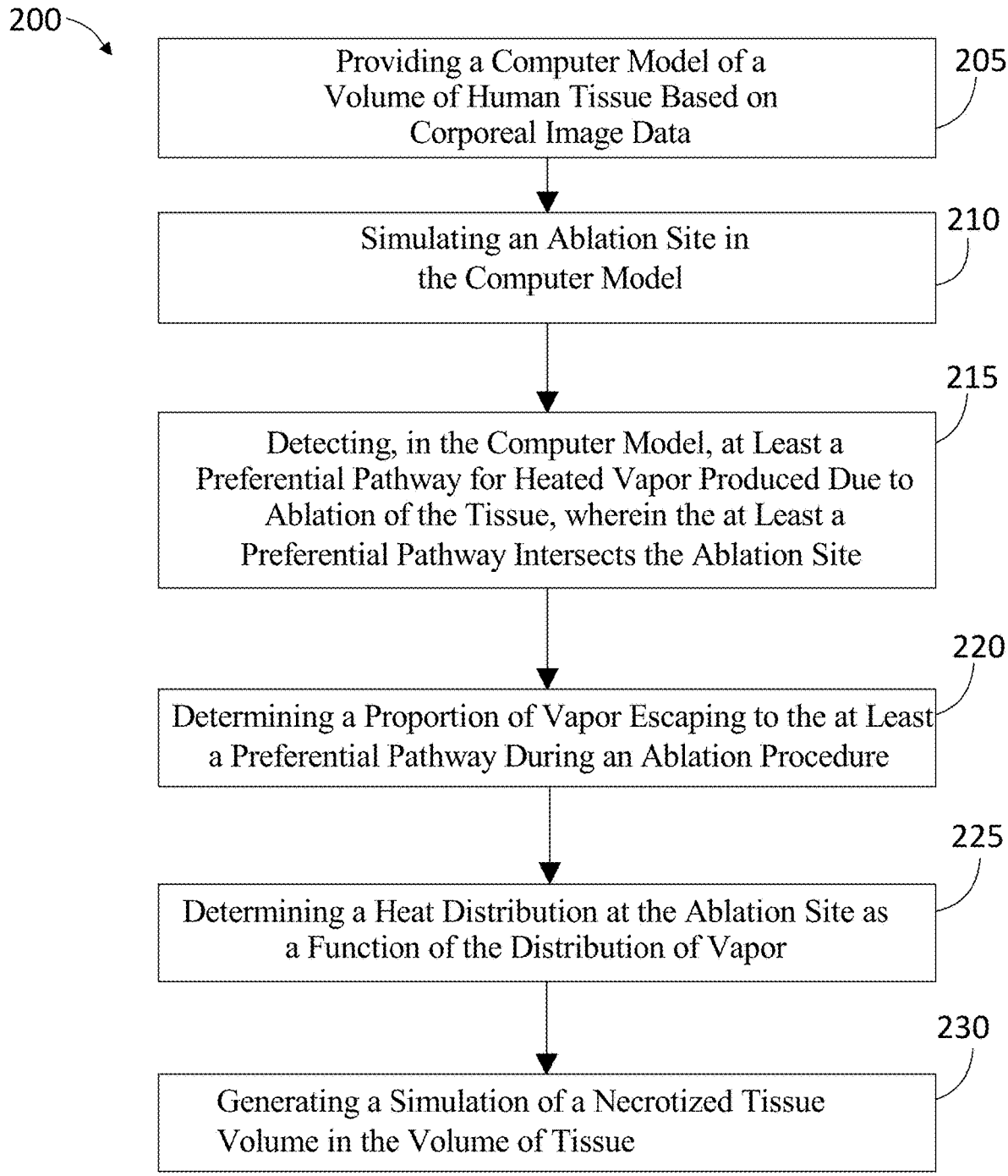
FIG. 2 is a flow diagram illustrating an exemplary embodiment of a method of modeling a necrotized tissue volume in an ablation procedure.

Referring now to FIG. 2, an exemplary embodiment of a method 200 of modeling a necrotized tissue volume in an ablation procedure is illustrated. At step 205, a radiology workstation 104 provides a computer model 108 of a volume of human tissue. Computer model 108 may include any graphical computer model 108 suitable for depiction of tissue, including without limitation organ tissue or regions of corporeal tissue in which an ablation procedure is to be performed, abnormal and/or pathological tissue to be removed, and/or a site or sites for location of ablative probes, and/or any graphical computer model 108 suitable for planning and/or guidance of procedures such as image-guided surgical procedures and/or ablative procedures as described in this disclosure, and/or any other use in systems and/or methods for medical imaging, planning of procedures, and/or image-guided medical procedures as may occur to a person skilled in the art upon reviewing the entirety of this disclosure. Computer model 108 may include one or more two-dimensional images and/or views and/or one or more three-dimensional images; two-dimensional and/or three-dimensional images may include a plurality of pixels, voxels, vector values, polygons, geometric primitives, or other data elements used to track, render, and/or depict two and/or three-dimensional images. One or more two and/or three-dimensional images may include component images; for instance, a three-dimensional image may include an assembly, collection, and/or plurality of two-dimensional images, such as "slices" as captured in imaging processes as described in this disclosure, which combine to create a three-dimensional image. Computer model 108 and/or radiology workstation 104 may be configured to generate and/or display a plurality of views, or displayed images based on the computer model 108, of the computer model 108 to a user, for instance in response to one or more user commands to modify a view angle and/or magnification of a displayed image generated from and/or using computer model 108; as a non-limiting example, a user may be able to rotate, pan, and/or zoom into or out of an image displayed based on computer model 108. As a further non-limiting example, user may be able to change a contrast level, color scheme, or displayed layer of computer model 108 as illustrated in a view. Where, for instance, computer model 108 is created by combination of image data captured using two or more medical imaging techniques, user may be able to modify view to show only one imaging technique; this may, for instance, enable user to view an image that emphasizes a particular feature such as a preferred pathway for vapor as described in more detail below, an area of abnormal and/or pathological tissue, and/or one or more organs or other identifiable anatomical features. Computer model 108 may be generated according to any process, process step, and/or combination of process steps that may occur to persons skilled in the art, upon reviewing the entirety of this disclosure, for generation of a computer model 108. Computer model 108 may include, without limitation, an anatomical model, which may include without limitation tumors, veins, arteries, and/or other anatomical structures; for instance, and without limitation, a computer model 108 of a liver may include a detailed anatomical model of the patient's liver parenchyma, tumors, hepatic vein, portal vein, and/or arteries.

Still referring to FIG. 2, radiology workstation 104 may generate computer model 108. Generation of computer model 108 may include reception and/or capture of one or more images of human tissue from and/or using at least a radiological machine 112. For instance, a three-dimensional surface and/or volume of an area of tissue, organ, or the like may be generated by a process of automatic or semi-automatic segmentation from two- or three-dimensional medical data. As a non-limiting example, a user may define seeds inside and outside each area of interest, such as parenchyma, tumors, hepatic vein, portal vein, and/or arteries in image data depicting a liver; an algorithm may subsequently automatically estimate and/or detect a boundary of a structure and/or area of interest. Algorithm to automatically estimate and/or detect a boundary of a structure and/or area of interest may include, without limitation, a random walker algorithm. Algorithm to estimate and/or detect a boundary may include, without limitation, a region growing algorithm. As a further non-limiting example, algorithm to estimate and/or detect a boundary may include, without limitation, a level set algorithm. Alternatively or additionally, a plurality of data entries describing past procedures may be used as training data, which may include any training data as described in further detail below, for instance correlating images with identifications entered by users or other systems and/or processes of boundaries, one or more pixels, voxels, and/or coordinates contained in and/or located at boundaries, or the like; boundary detection may be performed using any form of machine learning and/or deep learning as described in further detail below, including without limitation lazy learning, neural net processes, and/or generation of one or more machine-learning models. Such boundary identifications may be modified and/or improved by further user entries; for instance, a user may identify a point that an algorithm identified as within a structure and/or area of interest as outside the structure and/or area of interest, causing the algorithm to regenerate a boundary using the modified and/or additional information furnished by such an identification. Further continuing the non-limiting example, resulting segmentations may be combined and/or merged into a multi-label mask image, which may be used to generate a model made up of pixels, voxels, vector values, and/or geometric primitives, such as without limitation a tetrahedral multi-domain mesh. Such generated images may be overlaid on and/or combined with images captured from user data, including without limitation CT scans, MRI scans, or the like.

With continued reference to FIG. 2, generating a computer model 108 may further include imposing a virtual model of an organ over an image of tissue. For instance, and without limitation, preferential pathways may be difficult to view in image data such as data and/or models created using at least a radiological machine 112; as a non-limiting example, liver fissures, as thin interstitial spaces may offer low contrast to imaging, and spatial resolution of imaging modalities used to capture images of liver tissue may not be sufficient to capture them, making estimation of their location and/or geometry problematic. In an embodiment, a virtual model of an organ may be matched and/or registered to an image of tissue by detection of common features and/or anatomical structures; for instance, and without limitation, a virtual model of a lung and/or a portion thereof may be matched and/or registered to an image of a lung and/or portion thereof by lining up depictions in each of air passages such as bronchia and/or bronchial branches, barriers and/or membranes such as exterior surfaces of lungs, nearby bone and/or structure, major blood vessels such as pulmonary arteries, or the like. As a further non-limiting example, a virtual model of a kidney and/or a portion thereof may be matched and/or registered to an image of a kidney and/or portion thereof by lining up depictions in each of features such as ureters, elements of renal hilum such as without limitation renal vein, renal artery, and/or renal nerve, one or more interlobar blood vessels, renal pelvis, arcuate blood vessels, cortical blood vessels, pyramids, features of cortex, boundaries and/or features of capsules, and/or nearby bone and/or structure. As an additional non-limiting example, a virtual model of a breast and/or a portion thereof may be matched and/or registered to an image of a breast and/or portion thereof by lining up depictions in each of features such as, without limitation, nipples, major ducts, cooper's ligaments, small ducts and/or acini, lobes, and/or nearby feature such as chest wall, rips, and/or pectoralis muscle. As a further non-limiting example, a virtual model of a pancreas and/or a portion thereof may be matched and/or registered to an image of a pancreas and/or portion thereof by lining up depictions in each of features such as pancreatic ducts, bodies, heads, and/or tails, and/or external features such as bile duct, gallbladder, duodenum, and/or accessory pancreatic duct. As a further non-limiting example, a virtual model of a liver may be matched and/or registered to an image or combination of images of a person's liver by aligning images of outer surfaces, lobes, gall bladders and the like. Where a known orientation of image data for images captured from a patient is an attribute included in or with such image data, such known orientation may similarly be used to register such image data to a coordinate system or other orientation-sensitive datum included in or associated with a virtual model. Alternatively or additionally a user may manually align one or more virtual models with image data, for instance using drag-and-click or other techniques and/or facilities for user manipulation of virtual and/or computer images.

Still referring to FIG. 2, virtual model may be deformable; that is, virtual model may be able to modify dimensions and/or shapes of portions of the virtual model or of the entire model to match such dimensions and/or shapes to image data to which virtual model is being registered and/or matched; this may also be performed automatically and/or manually as described above. As a non-limiting and illustrative example, to model geometry of liver fissures a deformable liver model including information about the location of the fissures in a standard anatomy may be registered to and/or combined with image data depicting a liver of a patient; such fissures' geometry in the deformed model may be assumed to be indicative of true positions and/or geometries of fissures in the patient, and this information may be used in the evaporation/condensation modeling steps as described in further detail in this disclosure. Two or more modeling and/or imaging methods or techniques as described above may be combined to generate computer model 108.

Continuing to refer to FIG. 2, virtual model may be generated using image segmentation techniques to capture geometry of organs and/or important structures or regions of interest, including for instance the boundary of a liver, venous and arterial vascular trees, malignant tissues, and/or other organs and/or structures not involved in an intended ablation; such organs and/or important structures may include structures for which having a model and/or a 3D visualization may involve navigation of the surgical tools of the planning for optimal entry points, such as entry points that evade structures such as ribs, spine, lungs, and/or a gallbladder, which may either block or be damaged by a probe or other item inserted into a user's body. Identification of such structures may involve performance of a number of registration algorithms, such as without limitation algorithms based on region growing mechanisms, level set methods, graph cut methods, and/or based on Artificial Intelligence and/or Deep Learning approaches. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

With continued reference to FIG. 2, training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 2, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

As a non-limiting example, and continuing to refer to FIG. 2, training data used in any process in any example described herein may include entries correlating data suitable for use in any output sought in such a process with any input sought; in addition to any further examples that may be explicitly provided below, any process or process step as described below that analyses image, model, and/or medical process data and/or information, takes a geometrical feature and/or physical characteristic of any tissue as in input, and/or takes any power level, power delivery duration, choice of probe, choice of ablative process, or the like as an input, and generates outputs categorizing image and/or model data, identifying anatomical features of interest, identifying pathological and/or problematic tissue, identifying necrotized tissue, mapping or indicating boundaries of a preferential pathway as described below, and/or estimating distribution of vapor or power deposited thereby at any point and/or over any geometry identified and/or depicted in image and/or model data, may operate as any machine-learning and/or deep learning process as described herein, using training data correlating any such inputs to any such outputs.

Still referring to FIG. 2, a machine learning process or module, which may include any hardware and/or software module as described in this disclosure, may be designed and configured to generate at least an output by creating at least a machine-learning model relating inputs, such as data from medical and/or radiological images, to outputs, such as identifications of coordinates, coordinate sets, geometric figures, or other features indicating edges, boundaries, surfaces, and/or volumes of anatomical features of interest, pathological and/or problematic tissue, necrotized tissue, or any other characterization of tissue, as described herein, that may be used in any step of any embodiment of methods described in this disclosure; at least a machine-learning model may include one or more models that determine a mathematical relationship between inputs and outputs, which may be in any suitable form, and may accept scalars, vectors, matrices, or any other suitable mathematical object as inputs, outputs, and/or coefficient sets. Such models may include without limitation models developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, a machine-learning algorithm used to generate a machine-learning model may include, without limitation, linear discriminant analysis. A machine learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, any machine-learning module and/or modules may generate an output using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using any training data as described above; the trained network may then be used to apply detected relationships between elements of aeronautic excursion parameter data and weight capacity.

Still referring to FIG. 2, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use inputs as described above, outputs and described above, and a scoring function representing a desired form of relationship to be detected between inputs and outputs; scoring function may, for instance, seek to maximize the probability that a given input element and/or combination of input elements is associated with a given output element or output element set to minimize the probability that a given input element and/or combination of elements of input elements is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair. Persons skilled in the art, upon reviewing the entirety of this disclosure, will be aware of various possible variations of supervised machine learning algorithms that may be used to determine relation between aeronautic excursion parameters and weight capacity. In an embodiment, one or more supervised machine-learning algorithms may be restricted to a particular domain; for instance, a supervised machine-learning process may be performed with respect to a given set of parameters and/or categories of parameters that have been suspected to be related to a given set of weight capacity. Domain restrictions may be suggested by experts and/or deduced from known purposes for particular evaluations and/or known tests used to evaluate inputs and/or generate outputs. Additional supervised learning processes may be performed without domain restrictions to detect, for instance, previously unknown and/or unsuspected relationships between aeronautic excursion parameters and weight capacity.

With continued reference to FIG. 2, machine-learning algorithms may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, a machine learning module may perform an unsupervised machine learning process on corpus of training data, which may cluster data of training data according to detected relationships between elements of the training data, including without limitation correlations of elements of input data to each other and correlations of output data to each other; such relations may then be combined with supervised machine learning results to add new criteria for a supervised learning algorithm.

A machine-learning process may alternatively or additionally be designed and configured to generate at least an output by executing a lazy learning process as a function of the training data and one or more inputs. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" or heuristic of an output associated with at least an input, using training data. Heuristic may include selecting some number of highest-ranking associations. Machine learning algorithm and/or module may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure.

Still referring to FIG. 2, a model of an ablation site may further incorporate geometry of the ablation probe as deployed in the tissues. An ablation probe may be composed at list partially of flexible parts, such as without limitation tines in RF probes; these parts may be subject to deformation when deployed in the tissues, which may result in the final geometry of the deployed device differing from the original geometry of the device. Algorithms may be used for identifying and/or predicting a true geometry of a device as inserted to generate models of an ablation site which incorporate the true geometry of the deployed device or devices. Imaging sequences may be used to gather information about tissue parameters which affect ablation. For example, and without limitation, CT or MRI perfusion imaging sequences may be used to estimate perfusion point by point in the tissues, and this information can be incorporated into the model. Additionally parameters like the amount of fat and water per unit of volume may be imaged and incorporated into virtual model.

At step 210, and continuing to view FIG. 2, radiology workstation 104 simulates an ablation site in computer model 108. In an embodiment, simulating an ablation site may include identifying and/or marking one or more areas and/or elements of pathological and/or abnormal tissue, for instance as described above; a user may enter a command selecting the one or more areas and/or elements, for instance using a mouse, touchscreen, or other input device. A user may, for instance, "click" on, circle, mark, or otherwise delimit or indicate a location in the tissue depicted or modeled by computer model 108 as a location of abnormal and/or pathological tissue to be ablated. Simulation of an ablation site in computer model 108 may include identification of an area or volume of tissue to be necrotized, such as an area or volume containing abnormal and/or pathological tissue. A user may identify such an area or volume, for instance by drawing a line or series of lines around an area the user has identified for ablation; alternatively or additionally, radiology workstation 104 may generate a curve, volume, and/or surface representing a typical shape of tissue ablated using an ablative probe 124, which user may rotate, resize, and/or otherwise manipulate to encompass tissues the user has selected for ablation. A user may input a spatial extent of an ablation probe 124, a type of ablation, a duration of ablation, a desired dose, an indication of a spatial extent of a tumor or other area or element of abnormal and/or pathological tissue, an indication of a location in the area or element of abnormal and/or pathological tissue, an amount of power for ablation, a type of ablation device, a sequence of power, and/or other characteristic of the ablation or tissue. Various inputs may be automated. Instead of user input, radiology workstation 104 may provide any of the above information. Radiology workstation 104 may modify variables linked to a size and/or shape of ablated tissue; for instance, where a user enters a command and/or indication that a larger area of tissue is to be ablated, radiology workstation 104 may modify a variable describing a type or size of probe 124 to perform the ablation, a variable describing time and/or intensity of an ablative procedure, or the like. A user may have access to a discrete number of ablation probes, such as without limitation RF electrodes with diameters of 2 cm, 3 cm 4 cm. A user may, for instance in MW systems, have an option to select power from a finite number of power-level options and/or durations for which each power level may be employed; as a non-limiting example presented for illustrative purposes only, a user may enter instructions selecting power levels of 60 W, 100 W, 140 W to be deployed for 40 s, 60 s, and 80 s, respectively.

Still referring to FIG. 2, additional parameters that a radiology workstation 104 may modify, select, model, and/or use as inputs to any process described herein may include electrode size, for instance for RFA processes where tines may be deployed to generate an umbrella and this umbrella has a given diameter, power and duration of ablations, for instance for MW, where an ablation probe may look like a straight needle, and the user may change the applied power and the duration, a degree to which RF tines are extended into tissue, e.g. for a probe with slidably retractable tines, or the like. User and/or automated inputs may include a selection of at least a probe model, a selection of at least a power level, a selection of at least a duration of power to be supplied, and/or a selection of a number of overall ablations to be performed in a procedure.

As a further non-limiting example, radiology workstation 104 may modify a simulated probe 124 location and/or orientation as described below, in response to user commands modifying a shape or volume of tissue to be necrotized. Alternatively or additionally, radiology workstation 104 may split an area to be necrotized, as identified and/or modified as described above, into two or more simulated ablation sites as described in further detail below. In an alternative embodiment, a user may not indicate placement. Instead, the position is selected automatically based on the image data, such as by identifying a center of a tumor and/or an identified area and/or element of abnormal or pathological tissue. Various possible placements may be automatically identified and tested with separate simulations.

Still referring to FIG. 2, radiology workstation 104 may simulate a plurality of ablation sites. For instance, a user may indicate a sequence of placements for simulating sequential ablation operations or applications; such a sequence is simulated by repeating any step or steps as described in this disclosure for simulation of an ablation site, in any order or degree of repetition, for each sequential probe 124 position. Simulation of multiple ablation sites may be performed iteratively, for instance using results from a first simulated ablation site to simulate a second ablation site. Using modeling of tissue and/or cellular necrosis as described in further detail in this disclosure, modified tissue properties for various locations may be considered during the subsequent simulations. Sequential placement may be used for larger tumors, where the single probe 124 placement does not provide sufficient coverage of the ablated tissues volume to the tumor. In another possible implementation, a user may indicate multiple placements for simulating ablation using multiple devices at a same time; an aggregate thermal dose may be computed using a combination of individual thermal doses.

With continued reference to FIG. 2, simulating an ablation site may include simulating a probe 124 insertion. For instance, and without limitation, radiology workstation 104 may receive a user indication of a placement position of an ablation probe 124. Given anatomy, type of ablation, type of ablation device, or other limitations, the placement in the tissue may be limited. A user may indicate a possible placement of the ablation probe 124 by selecting a location or locations in computer model 108 of tissue. For example, a location in a multi-planar reconstruction of human tissue may be selected by a user using an input device, such as a mouse, touch screen, or the like. User may select an orientation of a probe 124 as well as a position; orientation may be selected according to a possible direction of insertion as dictated by anatomy, a desired location, shape, and/or size of area of tissue to be necrotized, or the like. As described above, radiology workstation 104 may alternatively or additionally select a probe 124 orientation based on a user-specified and/or automatically generated or selected shape and/or volume of tissue to be ablated; persons skilled in the art, upon reviewing the entirety of this disclosure, will be aware of various ways in which a shape and/or size of an area of ablated tissue may be associated with a direction of insertion and/or orientation of a probe 124. Where multiple ablation sites are simulated as described above, radiology workstation 104 may simulate a probe 124 insertion, including a position and/or orientation of an inserted probe 124, for each such ablation site. An image or model of an inserted probe 124 and/or a probe 124 in some stage of insertion may be superimposed on and/or combined with computer model 108 to effect the simulation.

At step 215, and still referring to FIG. 2, radiology workstation 104 detects, in the computer model 108, at least a preferential pathway for heated vapor produced due to ablation of the tissue. As used in this disclosure, a "preferential pathway" for heated vapor is a pathway that some heated vapor will travel down instead of diffusing through tissue as predicted in more naïve models; examples of preferential pathways are described in further detail below. For instance, and without limitation, vapor forming at an ablation site, under pressure created by the evaporation itself, may travel down pathways such as interstitial spaces, liver fissures, openings and/or paths created by insertion of probes, or the like, depositing heat along such pathways, for instance as dictated by physics of gas and fluid behavior under pressure. Preferential pathways may include, without limitation, interstitial spaces in the organs, ducts, tracks present in the tissues which may encroach an ablation site, and which represent a possible escape path for vapor. As vapor travels through preferential pathways, the vapor may encounter tissues at temperatures inferior to the evaporation temperature and release heat to these tissues and condense; this may result in a distribution of heat which may be determined by such factors as geometry of preferential paths where vapor travels. Radiology workstation 104 may detect that at least a preferential pathway intersects the ablation site, where "intersect" or "intersection" means as used herein that there is a way for some vapor to travel from the ablation site through the pathway instead of diffusing into tissue. For instance, and without limitation, a preferential pathway may intersect an ablation site where the preferential pathway passes through a region of tissue in which evaporation occurs, as described in further detail below. A preferential pathway may intersect an ablation site where the preferential pathway passes through an area where vapor diffuses through tissue, such that some vapor that has diffused through some tissue may be diverted along the preferential pathway. As a further non-limiting example, a preferential pathway may intersect an ablation site where the preferential pathway connects to another preferential pathway; for instance, and without limitation, a fissure or interstitial space may intersect or be intersected by a path of probe 124 insertion, such that vapor traveling along the path of probe 124 insertion may also escape into the fissure and/or interstitial space.

With continued reference to FIG. 2, detecting the at least a preferential pathway detecting, in the computer model 108, a depiction of an interstitial pathway intersecting a simulated ablation site. For instance, vapor forming at an ablation site, under the pressure created by the evaporation itself, may travel in interstitial spaces such as liver fissures and transport heat along the interstitial spaces. As a non-limiting and illustrative example, a liver is composed of multiple lobes which are separate but face each other; the interstitial space between two lobes is called a fissure. If an ablation site encroaches a fissure, the fissure may provide a path for vapor to escape local high pressure generated by heat of ablation; vapor may therefore travel in the fissure delivering heat to tissues that are facing the fissure. As a further non-limiting example, a preferential pathway may include a natural duct, such as without limitation a biliary duct. In an embodiment, detection of an interstitial pathway and/or other pathway such as a duct may be performed by detecting, in a virtual model of an organ, a pathway that intersects the ablation site. For instance, and without limitation, where a virtual model of an organ has been combined with other imaging data as described above to generate computer model 108, virtual model of the organ may include model information describing typical and/or probable locations of fissures; detection of the interstitial pathways may include detection of the typical and/or probable locations of interstitial pathways in the virtual model. This method of detection may enable radiology workstation 104 to detect preferential pathways in situation where imaging data makes detection challenging. As a non-limiting, illustrative example, in the specific case of liver fissures, as fissures are thin interstitial spaces and they offer low contrast to imaging; as a result detection in an image of human tissue may be difficult, as the spatial resolution of the imaging modalities available may not be sufficient to capture them. In the above example, a deformable liver model combined with and/or matched to computer model 108 may enable detection of likely location of fissures in a patient; likely location, even where not predicting an exact location of a fissure, may be sufficiently accurate to account for an effect of fissures, for instance by predicting that a fissure is likely intersecting the ablation site. Similarly, a model of another organ and/or another interstitial pathway may predict a likely encroachment and/or intersection of such a pathway with an ablation site, even where the exact location of such a pathway may not be determined.

Figure 3A:
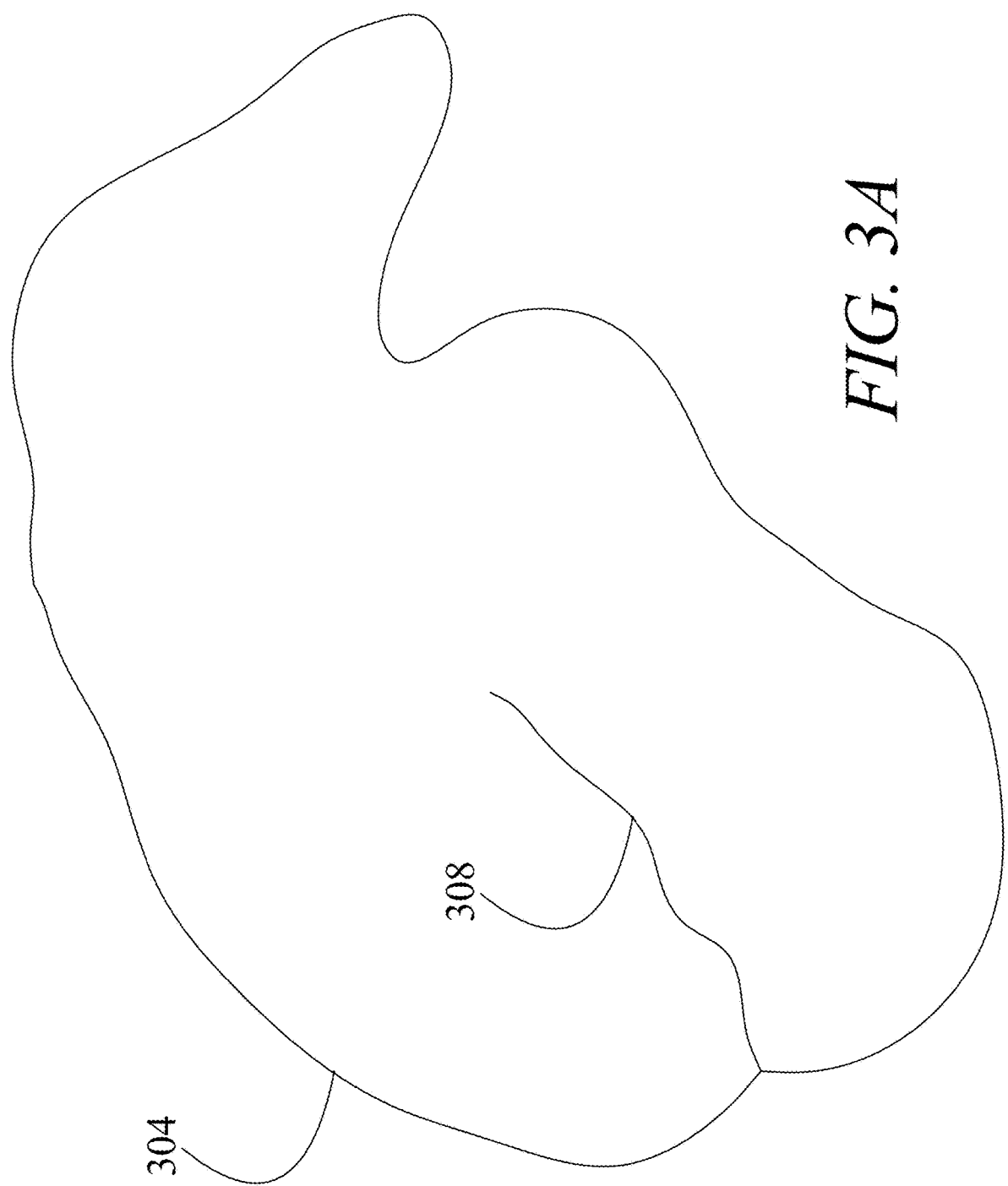
FIGS. 3A-C are schematic diagrams illustrating exemplary embodiments of computer models.
Figure 3B:
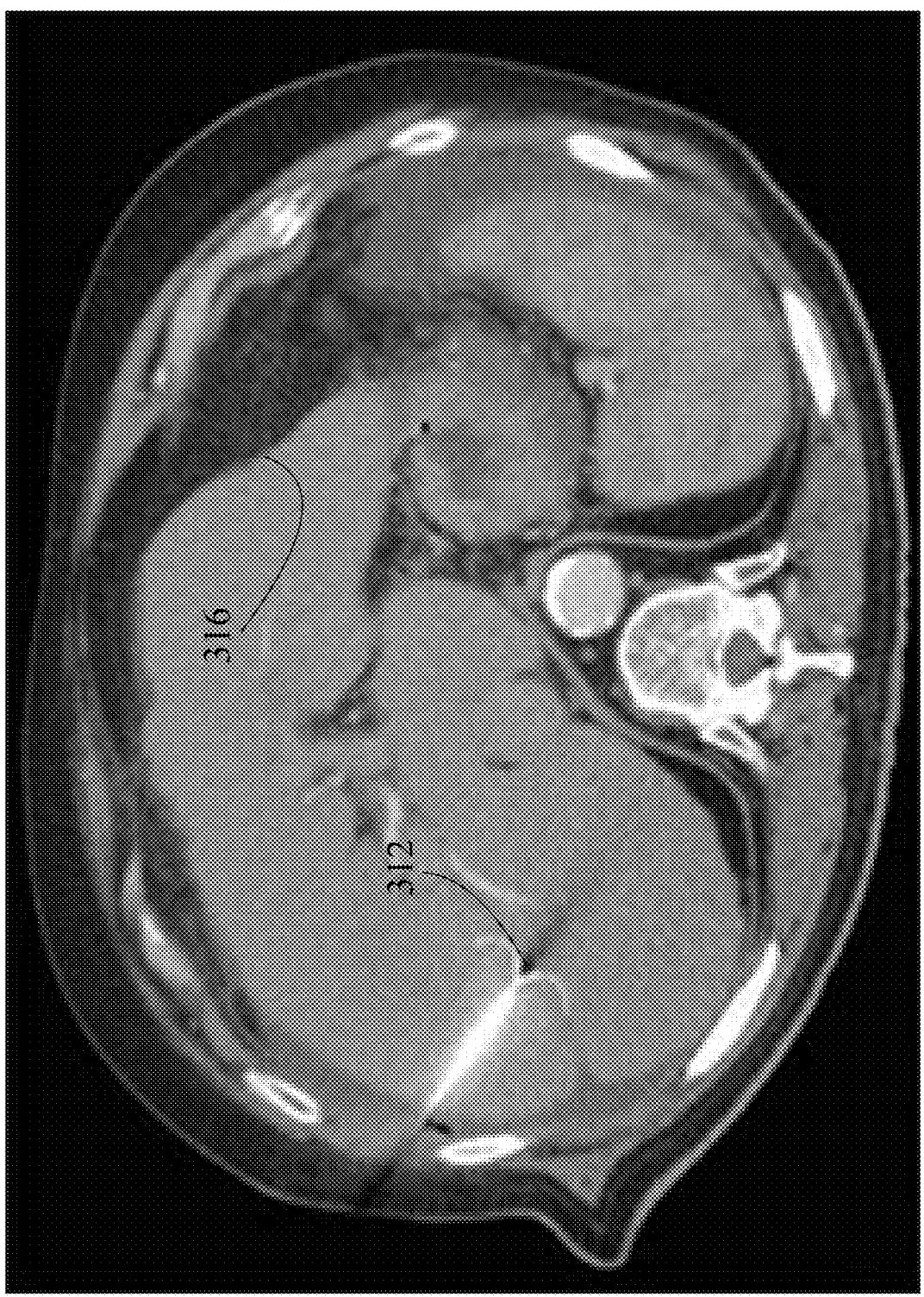
Figure 3C:
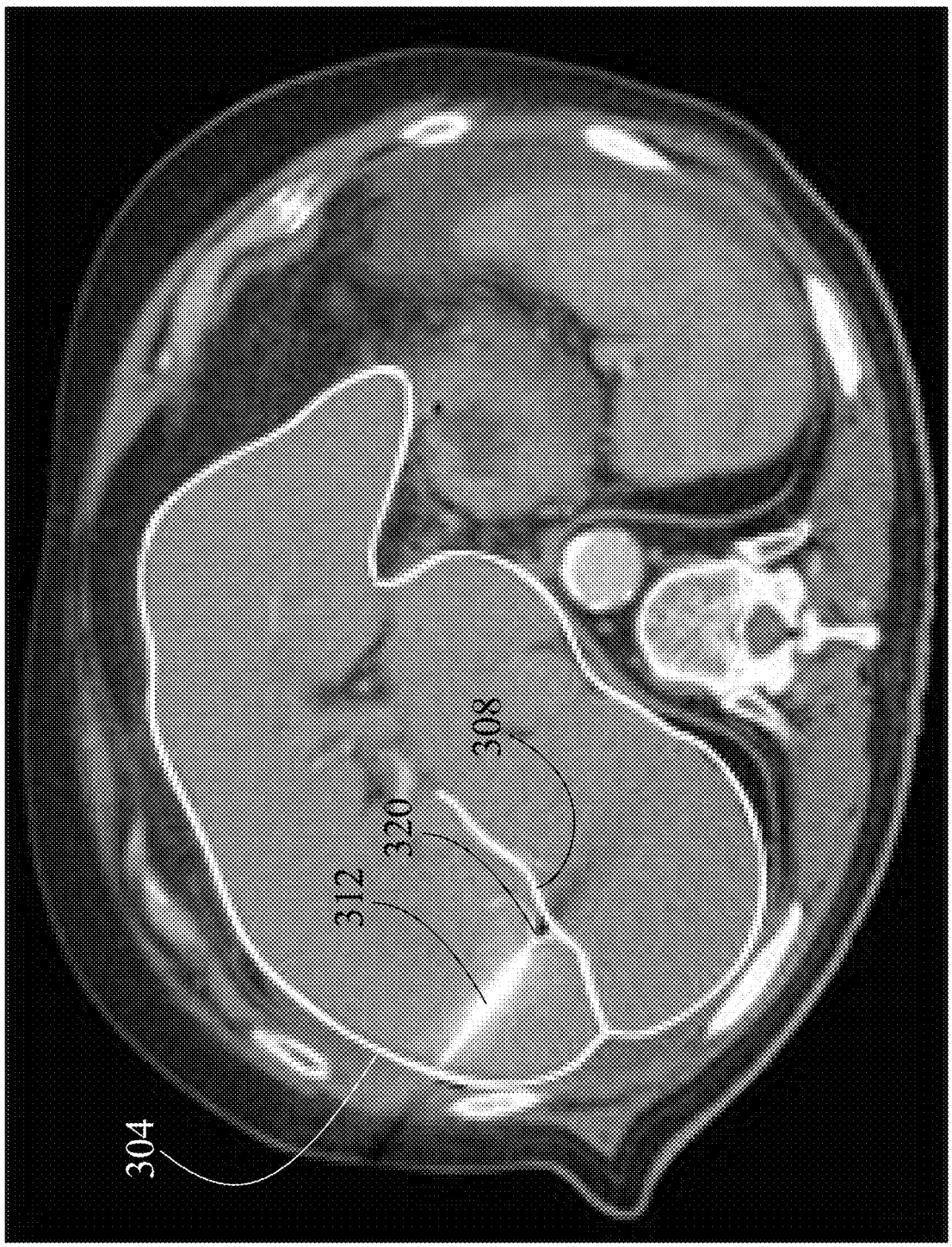

For instance, and without limitation, where tissues to be treated to ablation include liver tissues, a deformable liver model, as illustrated in FIGS. 3A, 3B, and 3C, may be used to estimate the geometry of the fissures of a liver. FIG. 3A illustrates a non-limiting exemplary embodiment of a model 304 of a liver; the model includes a representation of the geometry of a fissure 308 in the liver. FIG. 3B illustrates an exemplary embodiment of a CT image of a human liver, where an RFA electrode 312 has been deployed. In a non-limiting, exemplary embodiment, fitting a boundary of the deformable liver model 304 to a true liver boundary 316 available from CT images may enable radiology workstation 104 to update a shape of the liver model 304 in such a way that the deformed model accurately represents the liver. This in turn may allow determination of whether fissures 308 represented in model would encroach an ablation site 320 depicted in computer model 108.

Alternatively or additionally, and referring again to FIG. 2, detection of at least a preferential pathway may be performed using image enhancement substances 116 introduced into tissue. For instance, and without limitation, detecting a preferential pathway, such as without limitation an interstitial pathway as described above, may include introducing an image enhancement substance 116 into the ablation site, capturing an image of the ablation site with the image enhancement substance 116, and detecting the at least a preferential pathway as a function of the image of the ablation site. Introduction of image enhancement substance may include any suitable method for such introduction that may occur to persons skilled in the art upon reviewing the entirety of this disclosure, including ingestion, introduction via any metabolic pathway, introduction via intermediary organisms and/or autonomous devices, and/or injection, including without limitation injection using probe 124. Image enhancement substance 116 may include any image enhancement substance 116 as described above, including without limitation any contrast agent, fluorescent agent, and/or emissive agent. Probe 124 may include any suitable probe 124 for insertion and/or injection of agents into or at an ablation site, including without limitation a needle; probe 124 may, for instance, have an interior hollow or lumen through which image enhancement substances 116 may be forced under pressure, and at least an aperture at or near a tip of the probe 124 from which image enhancement substances 116 may be ejected and/or sprayed. Probe 124 may be and/or include a modified ablation probe 124, which may be modified to inject image enhancement substances 116. Radiology workstation 104 may subsequently capture images of human tissue including the image enhancement substances 116 via at least a radiological machine 112, and/or receive one or more such images from at least a radiological machine 112; image enhancement substances 116 may enter into preferential pathways, emphasizing such pathways and increasing their detectability and/or visibility in captured images. As a non-limiting and illustrative example, in order to make imaging of liver fissures possible and/or more feasible, a modified ablation needle may be used to inject high contrast liquids, gasses, or powders in the tissues, where these liquids, gasses, or powders penetrate fissures that encroach the ablation site, and render them visible in the images using high contrast properties of the injected liquids, gases, powders; this may allow radiology workstation 104 to capture geometry of the fissures by imaging, and to use this information for modeling the effects of vapor traveling in those fissures as described in further detail below.

Still referring to FIG. 2, detecting the at least a preferential pathway further comprises detecting a probe 124 insertion pathway. A "probe 124 insertion pathway," as used in this disclosure, is a pathway or track created in tissues by insertion of a probe 124, such as an ablative probe 124. For instance, and without limitation, where an ablative probe 124 is a needle or includes a needle-like form, insertion of the ablative probe 124 into tissues of a person may include puncturing the tissues in a linear direction, creating a track through which the probe 124 passes as it is inserted; vapor forming at the ablation site may travel in the track created in the tissues by the insertion of the ablation needle. Vapor may, as a non-limiting example, propagate in the interstitial space between the needle and the tissues for a certain length along the needle. This phenomenon may result in heating of a cylindrical region around the ablation needle, which is something not accounted for by current evaporation models. A length, position, and orientation of a track created by an ablative probe 124 may be known from images of volume of tissue, where the image captures the device as deployed in the tissues, or by using surgical instrument tracking technologies (e.g. electromagnetic, such the NDI Aurora system, or optic, such as the Medtronic StealthStation), which may indicate the position/orientation of the needle-shaped device in the tissues.

With continued reference to FIG. 2, radiology workstation 104 may estimate a distance the vapor will travel along the needle using; estimation may include, without limitation, matching one or more parameters of an ablation, which may include any parameters and/or images as described above, including without limitation any elements usable as inputs and/or outputs to any exemplary training data, any image characteristics of images and/or models, any user-selectable and/or automatically selectable options for any procedure involving ablation as described in this disclosure, and/or any parameters that may occur to persons skilled in the art upon reviewing the entirety of this disclosure, to one or more parameters of an previously performed procedure with regard to which the distance the vapor traveled along the needle may be recorded, which distance may be used as an estimate of a distance the vapor will travel in the current procedure. Matching may be performed with regard to multiple data entries listing multiple recorded and/or entered distances of vapor travel; this may be done using mathematical aggregation such as averaging by computing an arithmetic and/or geometric mean, or the like. Alternatively or additionally, a plurality data entries describing past procedures may be used as training data, which may include any training data as described above, and estimation may be performed using any form of machine learning as described above, including without limitation lazy learning, neural net processes, and/or generation of one or more machine-learning models. Processes for estimation, as described above, may be used to determine length of vapor travel along any preferential pathway, including any natural pathway such as fissures, ducts, or the like, as described above, based on any parameter and/or parameters as described above. Processes for estimation, as described above, may be used to determine a degree, volume, and/or distribution of necrotized tissue along any preferential pathway, including any natural pathway such as fissures, ducts, or the like, as described above, based on any parameter and/or parameters as described above. Any such estimations may alternatively and/or additionally be created based on user-entered instructions matching one or more parameters to estimated lengths of vapor travel and/or degree, volume, and/or distribution of necrotized tissue along any preferential pathway; such instructions may be based on user-derived empirical observations of distance of vapor travel and/or degree, volume, and/or distribution of necrotized tissue along any preferential pathway.

Continuing to refer to FIG. 2, detection of at least a preferential pathway may include detection of pathways generated by procedures, such as medical and/or surgical procedures. Such pathways may include insertion pathways and/or tracks of one or more probes, scopes, injection needles, biopsy needles, or the like. Pathways may include incisions, including both sutured and open incision. Pathways may include cavities generated using previous ablative or surgical procedures. Persons skilled in the art, upon reviewing the entirety of this disclosure, will be aware of various additional examples of preferential pathways that may be detected as described in this disclosure. Detection of probe 124-insertion pathways and/or pathways generated by procedures may be performed by modeling such procedures, such as modeling probe 124 insertion as described above and determining insertion tracks therefrom, or by detecting such pathways in images of patient tissue, such as images captured via at least a radiological machine 112.

Still referring to FIG. 2, detection of a preferential pathway may include detection of the preferential pathway in at least an image of tissue; this may be accomplished using any method for detection of shapes, structures, and or surfaces that may occur to persons skilled in the art upon reviewing the entirety of this disclosure. For instance, edge-detection may be employed to detect at least an edge of an interstitial pathway such as without limitation a liver fissure. Such detection may be enhanced by and/or combined with detection of pathways using images of patient tissue in which image enhancing substances have been injected, virtual images of organs as described above, or the like. Detection may alternatively or additionally include user inputs; a user may, for instance, visually identify a pathway and select and/or indicate a location of the pathway according to processes and/or procedures for user identification of surfaces and/or structures as described above. Automated processes may combine with user inputs to define surfaces and/or volumes of pathways according to processes as described above for detection of surfaces and/or structures. As a further non-limiting example, identification of one or more pathways may include displaying identifications to a user and receiving a user entry confirming identifications and/or negating such identifications; for instance, where radiology workstation 104 mistakenly identifies as a preferential pathway some other structure or element, a user may override the identification using a command indicating that the detected structure and/or element is not a preferential pathway.

With continued reference to FIG. 2, at step 220, radiology workstation 104 determines a proportion of vapor escaping to the at least a preferential pathway during an ablation procedure. In an embodiment, radiology workstation 104 may generate a predicted temperature distribution model; predicted temperature distribution model may include a model that predicts temperatures to which tissues are raised by the ablative probe 124 itself, discounting temperature effects of vapor. Vapor may be modeled as generated in a region identified as having temperatures above 100 degrees Celsius, where evaporation may occur. In an embodiment, regions of tissue heated to particular temperatures may be predicted using a bioheat equation, which may predict and/or account for effects of heat and/or evaporation in tissue. As a non-limiting exemplary embodiment, a bioheat equation may be of the form:

$$\rho c \frac{\partial T}{\partial t} = \nabla * k \nabla T + Q_{PWR} + Q_{PERF} + Q_E$$

where ρ is the tissue density, c is the tissue thermal capacitance, T is the temperature in the tissues, t is time, k is the tissue thermal conductivity, $Q_{PWR}$ is the dissipated power density resulting from applied ablative power, such as without limitation applied RF or MW power, $Q_{PERF}$ is the heat density lost to perfusion, $Q_E$ is the heat density lost to evaporation, or gained from condensation of vapor in the tissues, depending on tissue temperature at a particular point. The quantities ρ, k, c, T, $Q_{PWR}$ $Q_{PERF}$, and $Q_E$ are functions of space (scalar fields), while t, the variable indicating time, is a scalar quantity. The quantities ρ, k, c are properties of tissues, which can be considered as given fixed values, or as functions of temperature themselves. The term $Q_{PWR}$ models the power density, such as the RF or MW power density, applied by the RF/MW needle and dissipated in the tissues. This is a distributed heat source.

Still referring to FIG. 2, the perfusion term $Q_{PERF}$ is a power density that models the fact that a quantity of heat is lost to the capillary bed in the region around the ablation site. This loss occurs as the temperature of blood, which may be approximately 37° C., as a non-limiting example, is lower than the temperature reached by tissues during ablation, therefore an amount of heat will flow from the heated tissues to the capillaries, and later this heat will be taken away by the blood flow (perfusion). This term is therefore a distributed heat sink term. As a non-limiting example, blood flow in tissue may be simulated based on the patient-specific anatomical model of the tissue and/or of a vascular system; the blood flow through the vascular system may acts as a heat sink in diffusing the heat applying by an ablation probe 124. Blood flow in the patient-specific anatomic model may be simulated in order to provide a personalized modeling of the heat sink due to the blood flow. Locations of vessels in a tissue region, a size of the vessels, and/or other vessel characteristics may be used to model heat sink characteristics in a region of interest; the characteristics may be extracted from the segmented vessel information in the patient-specific anatomical model of the tissue and/or one or more organs of interest.

The $Q_E$ term is a power density that describes the effects of evaporation/condensation of water in the tissues. During an ablation, temperatures in excess of 100° C. may be reached in tissues at locations in the proximity of an ablation probe 124 and/or needle. At such locations a certain fraction of the water present in the tissues may evaporate. During the state change from liquid to gas the water may absorb a quantity of heat, known as "latent heat." Vapor may diffuse in the tissues, under the pressure it generates, and as it meets tissues at a lower temperatures the vapor may condense, and release in those lower temperature tissues the latent heat, along with any additional heat the vapor may have absorbed. The term $Q_E$ is therefore negative (heat sink) at locations where evaporation occurs (because heat is absorbed from tissues) and positive (heat source) at locations where the vapor condenses (because heat is released to tissues). A magnitude of the term $Q_E$ may depend, at any point in the tissues, on a rate of at which water is evaporating or condensing at that location.

In an embodiment, image processing device may determine regions in which evaporation occurs by reference to the above-described bioheat equation. In these regions the term $Q_E$ may be expressed as:

$$Q_E = -\alpha \frac{dW}{dt}$$

where α is the latent heat constant for water, W is the tissue water density, and t is time. This equation may apply at any point in the tissues where evaporation occurs, where $Q_E$ may represent the thermal power density absorbed from tissues. The total thermal power absorbed from tissues from evaporation at any instant in time, labeled for purposes of this disclosure as $Q_{E\_TOT}$, may be found by found by integrating the above equation over a volume that encapsulates all the tissues where evaporation occurs, and may be expressed as:

$$Q_{E\_TOT} = -\int \alpha \frac{dW}{dt} d\Omega$$

where Ω represents the region of tissues over which the integration is carried out.

In the above-described evaporation and condensation model, it may be assumed that $Q_{E\_TOT}$ may be re-distributed uniformly to tissues where the temperature is at a range within which condensation is predicted to occur; this range may include user-entered values, such as values empirically determined by a user and entered as an instruction to radiology workstation 104; as a non-limiting example for illustrative purposes, a user may enter a range of between 60° C. and 80° C., which may correspond to an empirically observed range within which tissues where condensation is likely to occur in tissues. Such a temperature range may alternatively or additionally be determined based on previous and/or experimentally evaluated procedures for which temperatures, condensation, and the like have been entered to produce training data and/or data to be mathematically aggregated as described above. FIG. 4 shows, as a non-limiting example, an RFA electrode 400, where a needle-shaped cannula 404 is able to release in the tissues a number of metallic filaments 408 which deploy in an umbrella-like fashion. These filaments are named "tines" and may be placed in electrical contact with tissues to permit encompassing and treating a larger volume of tissues. Exemplary thermal isolines are depicted, including an isoline 412 encompassing a volume of tissues heated at or above 100° C., an isoline 416 encompassing tissues heated at or above 80° C., and an isoline 420 encompassing tissues heated at or above 60° C. Any temperature isolines may be determined by machine-learning processes as described above, where isoline locations in images of past procedures as a function of parameters of such procedures, as provided at radiology workstation in the form of training data as described above. Alternatively or additionally, iso-lines may be generated using a bioheat equation as described above. For instance, and without limitation, given a temperature field T computed via a bioheat equation, isolines may be computed using a marching squares algorithm in two-dimensional images and/or models and/or a marching cubes algorithm in three-dimensional images and/or models. Persons skilled in the art, upon reviewing the entirety of this disclosure, will be aware of various ways in which a bioheat equation may be used to determine and/or compute tissue temperature isolines, each of which is contemplated as within the scope of the instant disclosure. Evaporation may occur in the volume enclosed by the 100° C. isoline 412, and condensation may occur in the volumes enclosed in an area for condensation as described above, estimated using any process as described above for determination of a condensation area, such as an area between isolines at upper and lower ends of a condensation temperature range; as an illustrative, non-limiting example, this may be between 80° C. and 60° C. isolines 416, 420. An evaporation model may be summarized therefore as follows: in the evaporation region defined by T>100° C., $$Q_E = -\alpha \frac{dW}{dt};$$

in the condensation region, $Q_E = Q_{E\_TOT}/\text{Vol}_{.60,80}$; and in any other region $Q_E = 0$.

Returning to FIG. 2, temperature predictions may further predict a volume and/or pressure of vapor produced as a function of a temperature of the tissues, a length of time during which the tissues are kept at such a temperature, and/or an estimated moisture content of the tissues. Radiology workstation 104 may predict a proportion of vapor that will be distributed to the at least a preferential pathway based on vapor pressure and/or volume in combination with geometry of the at least a preferential pathway; prediction may be based on a user-entered empirical value and/or on a value estimated using any machine-learning processes as described above. Radiology workstation 104 may model geometry of at least a preferential pathway using any procedure, method step, and/or any combination of procedures and/or method steps as described in this disclosure for determining shapes and/or sizes of structures and/or surfaces. For instance, radiology workstation 104 may identify an interior surface of a pathway such as a fissure or other interstitial pathway and calculated a surface area of the interior surface using any suitable method for computing a surface area from an image of a surface. Radiology workstation 104 may alternatively or additionally determine a volume of a preferential pathway using any suitable computational method for calculation and/or estimation of volumes in computer images.

In an embodiment, and still referring to FIG. 2, determining a distribution of vapor to the at least a preferential pathway may include determining a flow rate of vapor into the at least a preferential pathway, and determining the distribution of vapor to the at least a preferential pathway as a function of the flow rate. For instance, physical laws, such as without limitation the ideal gas law, governing behavior of gasses may be used to determine a pressure level of vapor, and a flow of vapor through and/or into at least a preferential pathway based on aperture size of the at least a preferential pathway. Determining the distribution of vapor as a function of the flow rate may include determining a rate of vapor generation, comparing the flow rate to the rate of vapor generation, and determining the distribution of vapor to the at least a preferential pathway as a function of the comparison. Radiology workstation 104 may alternatively or additionally determine distribution of vapor by determining an evaporation rate and/or a condensation rate of vapor. In an embodiment, each of flow rate, evaporation rate, and/or condensation rate may be determined using data from past operations and/or user-entered data, which may be matched to a current operation by querying stored data records and/or by using such data as training data as described above. Alternatively or additionally, distribution of vapor based on flow rate, condensation rate, and/or evaporation rate may be determined using machine-learning algorithms based on training data, as described above correlating distribution of vapor to flow rate, condensation rate, and/or evaporation rate. In an embodiment, rate of flow and/or proportion of vapor distributed to preferential paths may be determined during an ablation procedure using temperature sensing methods; temperatures sensed at various points in a preferential path, at ablation site, or at other points in tissue may be used to estimate vapor distribution to and/or from the various points, either by user instructions describing a relation between sensed temperatures, as well as any other parameters of ablation procedures as described above, and vapor distribution, or by generating training sets correlating sensed temperatures to necrotized tissues as determined after a procedure, and using machine-learning processes as described above to determine a relationship between temperatures and vapor deposition and/or loss at various points. Temperature-sensing technology may include temperature sensors inserted into subject tissue, including temperature sensors incorporated in or attached to probe 124 and/or separately inserted temperature sensors; for instance, temperature sensors along a shaft of the probe 124 may detect how the temperature along the shaft changes during an ablation procedure, which may be used to determine how far along the shaft vapor travels and/or how much vapor travels to a given point along the shaft. Temperature sensors may likewise be placed at one or more locations along other preferential paths. Alternatively or additionally, MRI thermometry may be used to capture temperatures in preferential paths and estimate vapor flow in the paths for the. Alternatively or additionally, equations containing b may be compared to image data from post-procedure images taken using any imaging technology as described above, including without limitation T1 weighted MRI imagery, where equations may be used to predict a quantity and/or volume of necrotized tissue using any methods for estimating and/or calculating a volume of necrotized tissue as described above, and an error function may be generated using actual necrotized tissue volumes; minimization of error function may be performed using any machine-learning algorithm as described above, and/or by estimations entered by users.

Alternatively or additionally, and still referring to FIG. 2, determining the distribution of vapor to the at least a preferential pathway may include deriving a surface area of the at least a preferential pathway and determining the distribution of vapor as a function of the surface area. Determination of surface area of the at least a preferential pathway may be performed as described above. In an embodiment, determination of distribution of vapor may include modeling uniform distribution of vapor over surfaces of all pathways of at least a preferential pathway and/or all surfaces of ablation site. Alternatively or additionally, where a quantity of vapor diverted to at least a preferential pathway is estimated using pressure or the like as described above, determination distribution over a surface area of at least a preferential pathway may include, without limitation, uniform distribution over the surface area of the diverted quantity. As described in further detail below, distribution of vapor may be used to determine a distribution of vapor condensation power, which may represent a power per unit of area and/or volume the vapor deposits to tissues during condensation.

As a further non-limiting example, and with continued reference to FIG. 2, determination of distribution of vapor to the at least a preferential pathway may include deriving a volume of the at least a preferential pathway and determining the distribution of vapor as a function of the volume. Deriving volume of at least a preferential pathway may include any process and/or process steps, in any order or degree of repetition, suitable for estimation of volume of a structure as described above. Determination of distribution of vapor to the at least a preferential pathway as a function of volume may include modeling uniform distribution of vapor throughout volumes of all pathways of at least a preferential pathway and/or all volume of ablation site. Alternatively or additionally, where a quantity of vapor diverted to at least a preferential pathway is estimated using pressure or the like as described above, determination distribution over a volume of at least a preferential pathway may include, without limitation, uniform distribution over the volume of the diverted quantity.

In an alternative or additional embodiment, and still referring to FIG. 2, determination of distribution of vapor to the at least a preferential pathway may include determination that a constant proportion and/or amount of vapor is so distributed; constant may be stored in memory of radiology workstation 104. In an embodiment, radiology workstation 104 may retrieve a constant corresponding to a given pathway from a table of constants; table of constants may list proportions of vapor diverted to preferential pathways that correspond to one or more descriptors of preferential pathways, where one or more descriptors may include total volume of preferential pathways, number of preferential pathways, aperture openings at preferential pathways, or the like. For instance, and without limitation, a constant b=0.2 may represent that 20% of vapor is redistributed along a probe 124 insertion track.

At step 225, and still referring to FIG. 2, radiology workstation 104 determines a heat distribution at the ablation site as a function of the distribution of vapor. In an embodiment, determining the heat distribution at the ablation site may include identifying a proportion of heat converted to vapor, and determining the heat distribution at the ablation site as a function of the proportion of the heat converted to vapor and the distribution of vapor to the at least a preferential pathway. This may be accomplished, without limitation, by using a modified bioheat equation, as described above in which $Q_{E\_TOT}$ is replaced with a quantity (1-b) $Q_{E\_TOT}$ of thermal power is redistributed to the tissues uniformly as vapor, where the scalar b is in the range 0 to 1 and represents the proportion of vapor redistributed to the at least a preferential pathway. (1-b) $Q_{E\_TOT}$ may be redistributed to those tissues having a temperature between a lower and a higher specified threshold (e.g. 60° C. and 80° C.) as modeled by a bioheat equation as described above, by way of diffusion and condensation in tissues similarly to processes as described above. In this manner, radiology workstation 104 may calculate a distribution of heat transferred to tissue by the vapor.

In an embodiment, and still referring to FIG. 2, radiology workstation 104 may further determine a distribution of heat to surfaces of one or more preferential paths; for instance, a quantity b $Q_{E\_TOT}$ of power transferred by vapor may be redistributed along those surfaces, or in those volumes, representing the preferential paths where vapor travels and condenses (tracks, ducts, interstitial spaces, holes), where b as above represents the proportion of vapor diverted to the at least a preferential path. This may model effects of heat which is transported and released by condensing vapor to those locations. For instance, where at least a preferential pathway includes a probe 124 insertion track, power b $Q_{E\_TOT}$ may be modeled as uniformly distributed in a cylindrical region around a shaft of the probe 124, accounting in this way for heating that occurs in such region due to vapor traveling in the interstitial space between the probe 124 shaft and tissues.

As a further non-limiting example, and continuing to refer to FIG. 2, where a probe 124 is modeled encroaching a liver fissure, a portion of the total thermal power absorbed by vapor b $Q_{E\_TOT}$ should be delivered to the surfaces of the fissure of the ablation site, where b as before represents a proportion of vapor diverted to the preferential pathway, such as the fissure. Fissure volume may be estimated using any process as described above, including, as a non-limiting example, using machine-learning processes as described above, and/or by edge detection procedures or the like.

Figure 5A:
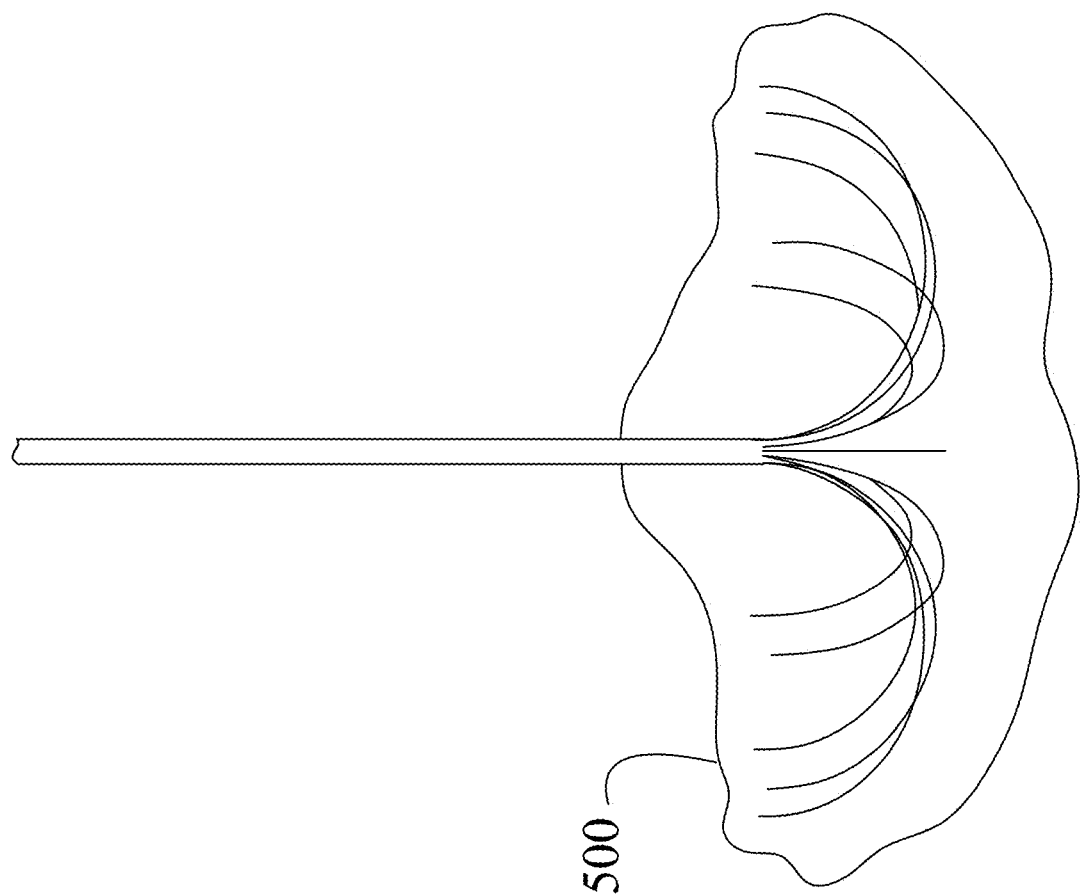
FIGS. 5A-D are schematic diagrams illustrating exemplary embodiments of volumes of necrotized tissue.
Figure 5B:
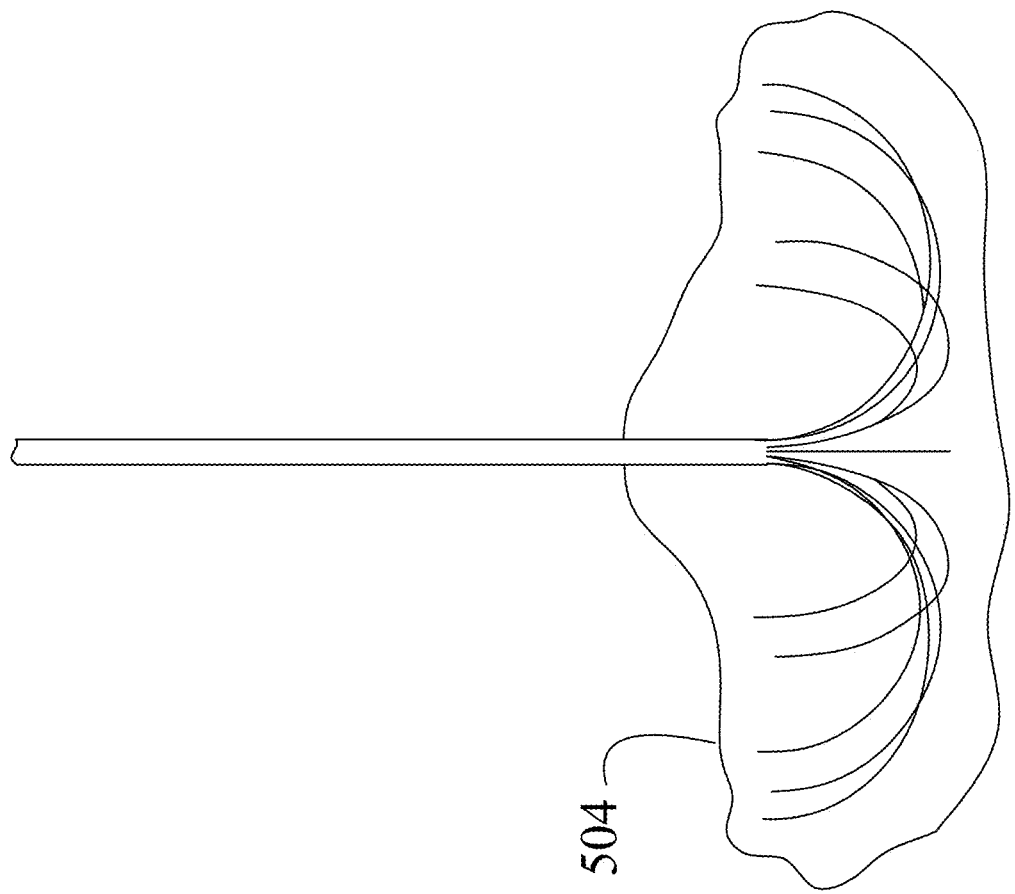

At step 230, and still referring to FIG. 2, radiology workstation 104 generates a simulation of a necrotized tissue volume in the volume of tissue; the simulation of the necrotized tissue volume represents a volume of tissue necrotized by heat during an ablation procedure performed at the ablation site. Generating the simulation of the necrotized tissue volume further comprises simulating a primary ablation volume as a function of heat energy present at the ablation site, where the "primary ablation volume," as used in this disclosure, is the volume of tissue by heating and diffusion through tissues from the ablation site, and excludes tissues necrotized as a result of diversion of vapor through preferential pathways. In an embodiment, this may be performed by using a modified bioheat equation, as described above, to determine isolines and/or surfaces representing boundaries of regions heated to a minimum temperature for necrotization of tissues; using a reduced (1-b) $Q_{E\_TOT}$; for instance, an isoline or surface within which all tissues are at or above 60 degrees Celsius may be identified. This may, in a non-limiting example, result in a reduced primary ablation volume, because a lesser quantity of heat energy may be deposited in such tissues. For instance, and without limitation, FIG. 5A illustrates an exemplary embodiment of a predicted primary ablation volume 500 according to existing methods; FIG. 5B illustrates an exemplary embodiment of a primary ablation volume 504 modeled according to a reduced (1-b) $Q_{E\_TOT}$. Alternatively or additionally, necrotization may be modeled using an Arrhenius model that looks at temperature and time of exposure to a given temperature. In an embodiment, a bioheat equation may be used to calculate a temperature at each point in an ablation site, and the temperature may be computed at discrete time intervals, such as without limitation every 1 second during a 6 minutes ablation). For each point a temporal evolution of the temperature may be fed to the Arrhenius model which may indicate a 0 to 100% probability of cell death for that point of tissues; the ablation/necrotized tissue volume may be taken to be a volume of tissue estimated to have 90% death probability. Alternatively or additionally, a plurality of data entries describing past procedures may be used as training data, which may include any training data as described in further detail above, for instance any procedural and/or modeled parameters, outputs, or the like as described in this disclosure, including without limitation power level and/or temperature delivered to a given site, two or three-dimensional depictions of ablation sites, or the like with identifications entered by users or other systems and/or processes of necrotized tissues, one or more pixels, voxels, and/or coordinates contained in and/or located at necrotized tissues, or the like; prediction of necrotized volumes may be performed using any form of machine learning and/or deep learning as described in further detail below, including without limitation lazy learning, neural net processes, and/or generation of one or more machine-learning models.

Generating a simulation of the necrotized tissue volume may include simulating necrotized tissue along the at least a preferential pathway. This may be determined by, for instance, distributing vapor diverted along the at least a preferential pathway to a surface area of tissues along the at least a preferential pathway. Distribution to a surface area may include uniform distribution of distributed proportion of vapor to all surface areas; in this case $bQ_{E\_TOT}$ may be assumed to be spread over the surface area; $bQ_{E\_TOT}$, so distributed, may be treated as a heat source at each point along the surface, permitting prediction of a volume of adjacent tissue that will be heated to the point of necrotization, for instance using a bioheat equation as described above. Distribution of $bQ_{E\_TOT}$ to any particular point on a surface of a preferential pathway, may depend on vapor flow and resulting convective and conductive heat exchange with the surface, and on the rate of condensation of vapor at that point; this may be estimated and/or determined using machine-learning as described above, finding relationships between proportion of vapor entering a preferential path and temperature at points along preferential path or the like.

Figure 5C:
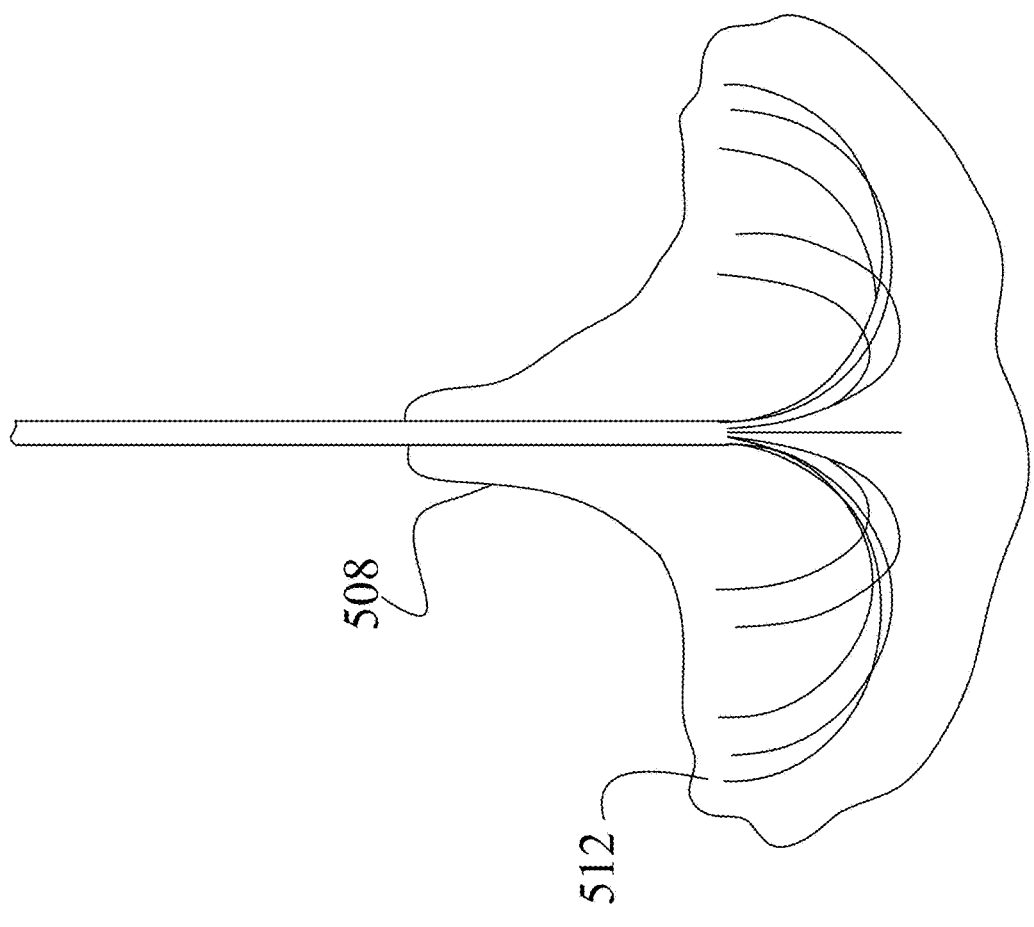
Figure 5D:
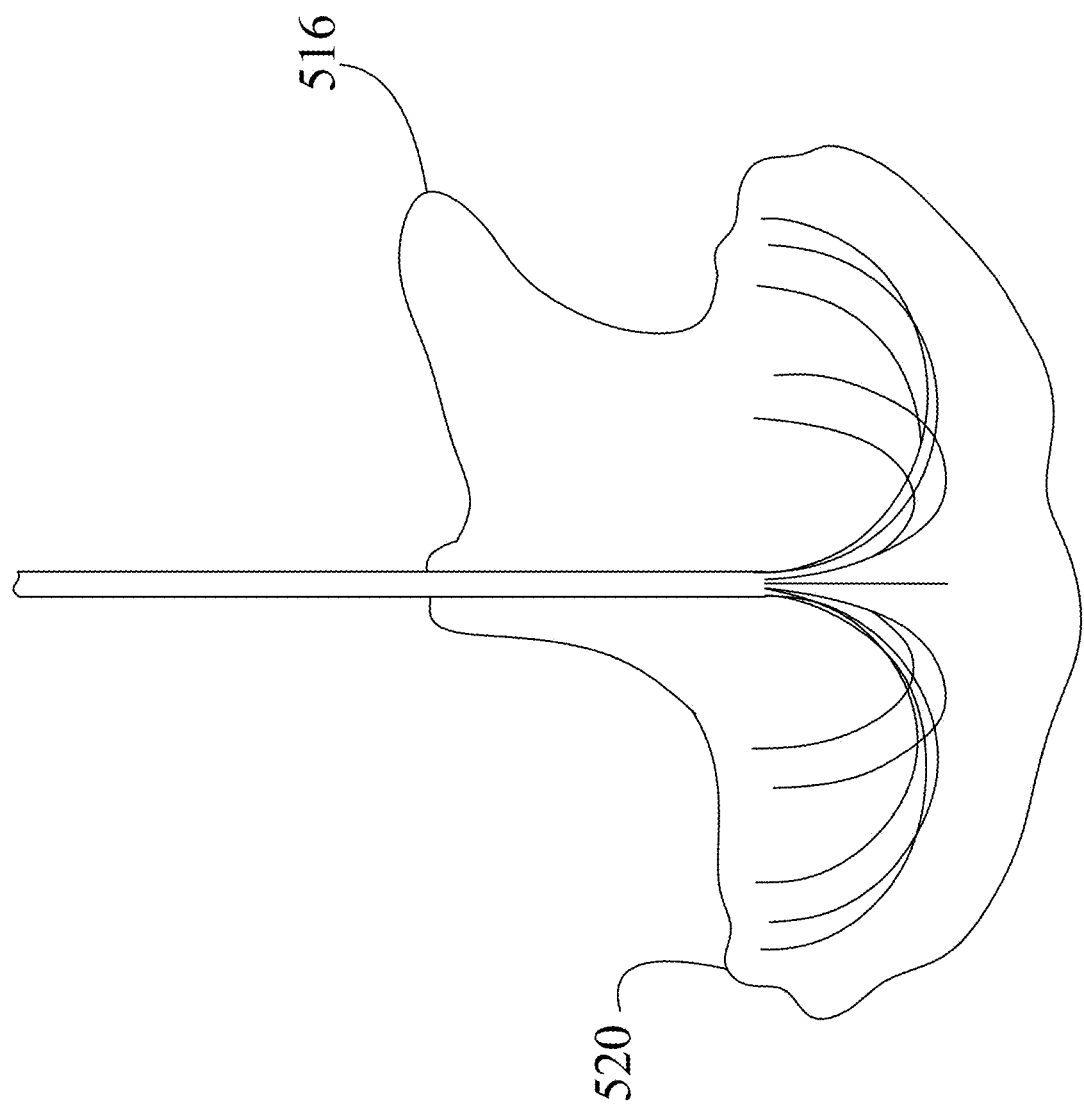

As a non-limiting example, FIG. 5C illustrates an exemplary embodiment of an ablation volume estimated with a model wherein a proportion of vapor is simulated as escaping along an insertion path of a probe 124. In this exemplary embodiment, a thermal power b $Q_{E\_TOT}$, with b=0.2, may be redistributed to a cylinder aligned to the electrode shaft, where the cylinder starts at the point where the shaft connects to the tines; cylinder may have, as a non-limiting example, a height of 2 cm. The remaining power (1-b) $Q_{E\_TOT}$ may distributed, as described above, to tissues with temperatures between 60° C. and 80° C. As shown, a top 508 of a resulting ablation volume 512 may be more elevated compared to the predictions as shown in FIG. 5A, due to an additional section of necrotized tissue along the insertion path. FIG. 5D illustrates an additional case, where an interstitial pathway (not shown) extends to one side of the probe 124, resulting in a plume 516 of necrotized tissue that, in this exemplary embodiment, causes an overall ablated volume 520 to have an irregular shape.

Figure 6A:
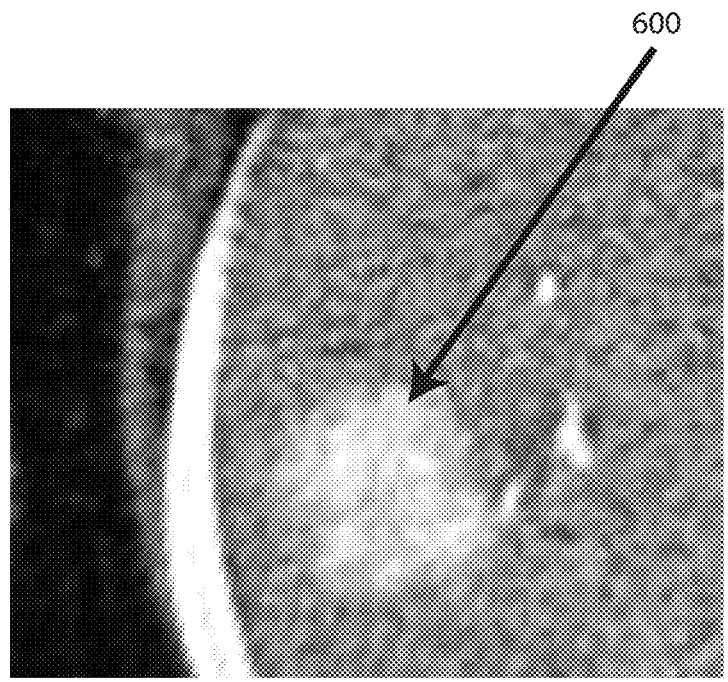
FIGS. 6A-B are schematic diagrams illustrating an exemplary embodiment of a display depicting a volume of necrotized tissue.
Figure 6B:
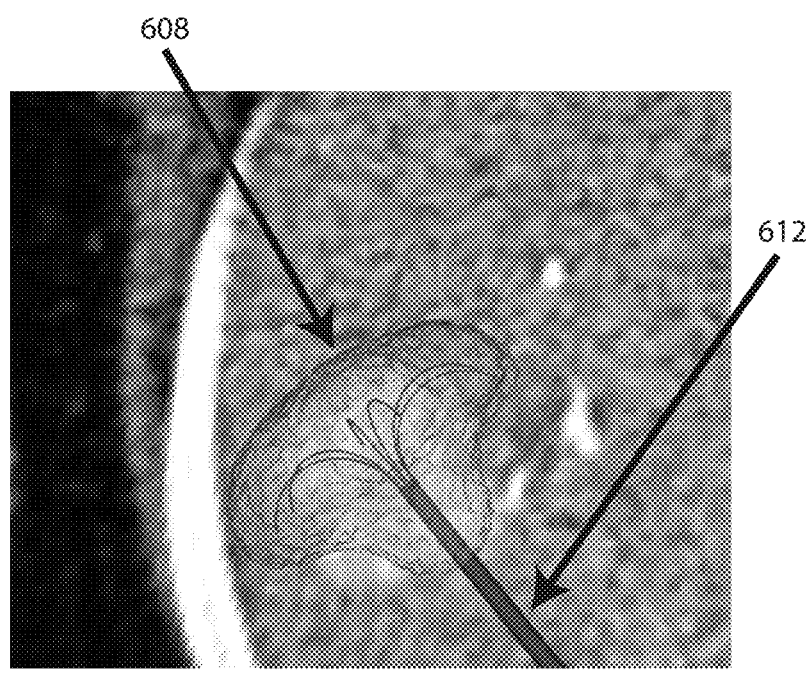

Referring again to FIG. 2, in an embodiment, radiology workstation 104 may display simulation of volume of necrotized tissue to a user. As a non-limiting example, radiology workstation 104 may display simulated volume of necrotized tissue combined with and/or superimposed on computer model 108. FIG. 6A illustrates a non-limiting example of a computer model of human tissue showing an ablation site 600. FIG. 6B depicts a non-limiting illustration of a computer model as in 6A, including a visual representation of an ablation probe 604 inserted at an ablation site, and a simulation 608 of a volume of necrotized tissue. Simulation 608 may be generated using any method, method step, or combination of methods for generation of a computer model 108 as described above; for instance, and without limitation, any view of computer model 108 may be modified using simulation to depict a corresponding view of simulation 608.

Referring again to FIG. 2, radiology workstation 104 may generate one or more messages to a user based on the above-described detection and/or simulation steps. For instance, and without limitation, a message may be generated upon detection of one or more preferential pathways intersecting an ablation site, warning of the presence of the one or more preferential pathways; in an embodiment, a physician is simply warned that the current ablation site encroaches a fissure or other pathway and that the ablation geometry may be altered by the presence of the fissure or other pathway. Such a warning may, in an embodiment, be performed instead of simulating the necrotized volume; alternatively, simulated volume may be presented to a physician in conjunction with a message identifying one or more preferential pathways, to enable the physician to assume a wider margin of error in performing ablation, or to alert the physician to a possibly ineffective procedure so the procedure may be revised. Radiology workstation may, for instance, compare a simulated volume to a volume of tissue intended to be necrotized; the comparison may be used to inform a medical professional such as a physician regarding differences, such as a simulated volume indicating that the volume of tissue intended to be necrotized may not be fully necrotized. Embodiments of method 200 and/or one or more steps thereof may be repeated two or more times; for instance, in the context of intraoperative guidance, method 200 may be used to aid physicians in evaluating of which tissues are treated and which not by a particular ablation directly in the operating room, offering a "see-and-treat" functionality. For instance, and without limitation, method 200 may be combined with image-guided surgical methods to provide a physician with a high degree of accuracy when performing each ablation, assessing the results, and performing each subsequent ablation.

Figure 7:
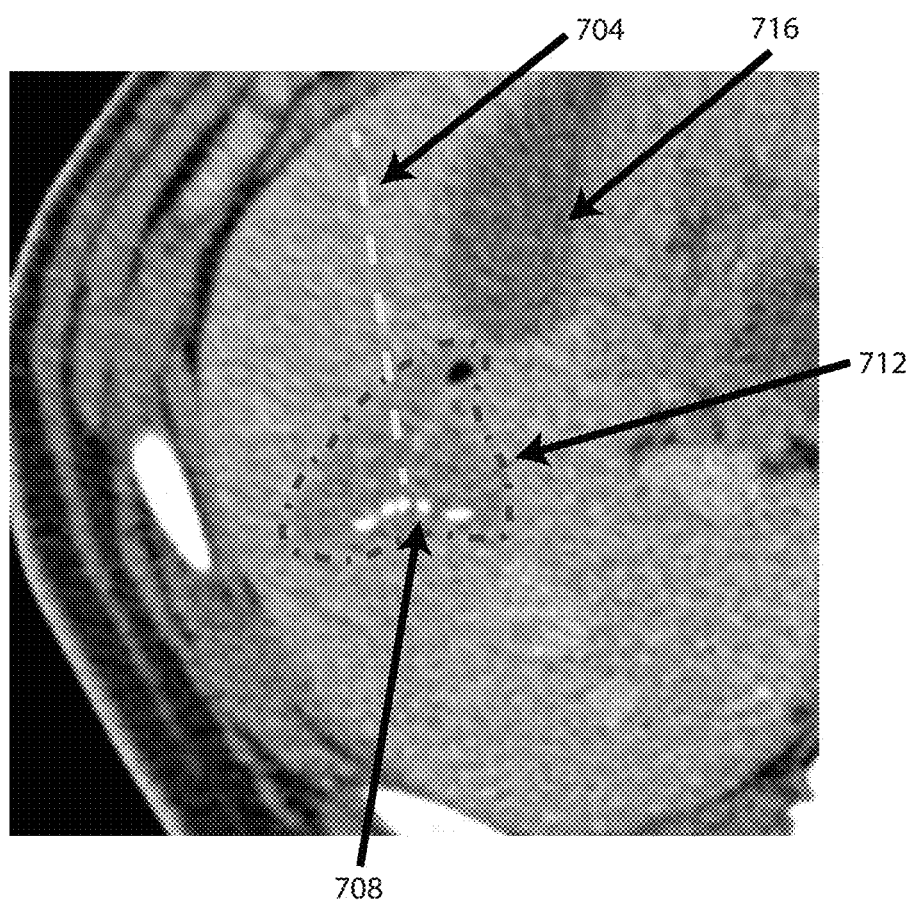
FIG. 7 is a CT scan image illustrating an exemplary embodiment of a volume of necrotized tissue.

FIG. 7 illustrates a non-limiting example provided for contextual purposes only, of a CT image of an ablation performed via percutaneous liver RFA in a pig that was affected by fissure presence. A dashed line 704 indicates a position and orientation of an RFA electrode shaft (not visible as the imaging plane does not intersect it). Bright dots 708 indicate the position of the tines of RFA electrode, as they intersect an imaging plane of CT image. A dash-dotted line 712 highlights a contour of an ablation, where necrotized tissues are visible in a darker shade of gray. A dark feature 716 indicates a gallbladder; in this specific and non-limiting example of an ablation, a fissure that connects the ablation site to gallbladder allowed vapor to escape the ablation site by traveling in the fissure towards the gallbladder. As a result the ablation is asymmetrical with respect to the electrode shaft, and the ablation has a "plume" shape that bends towards the gallbladder.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
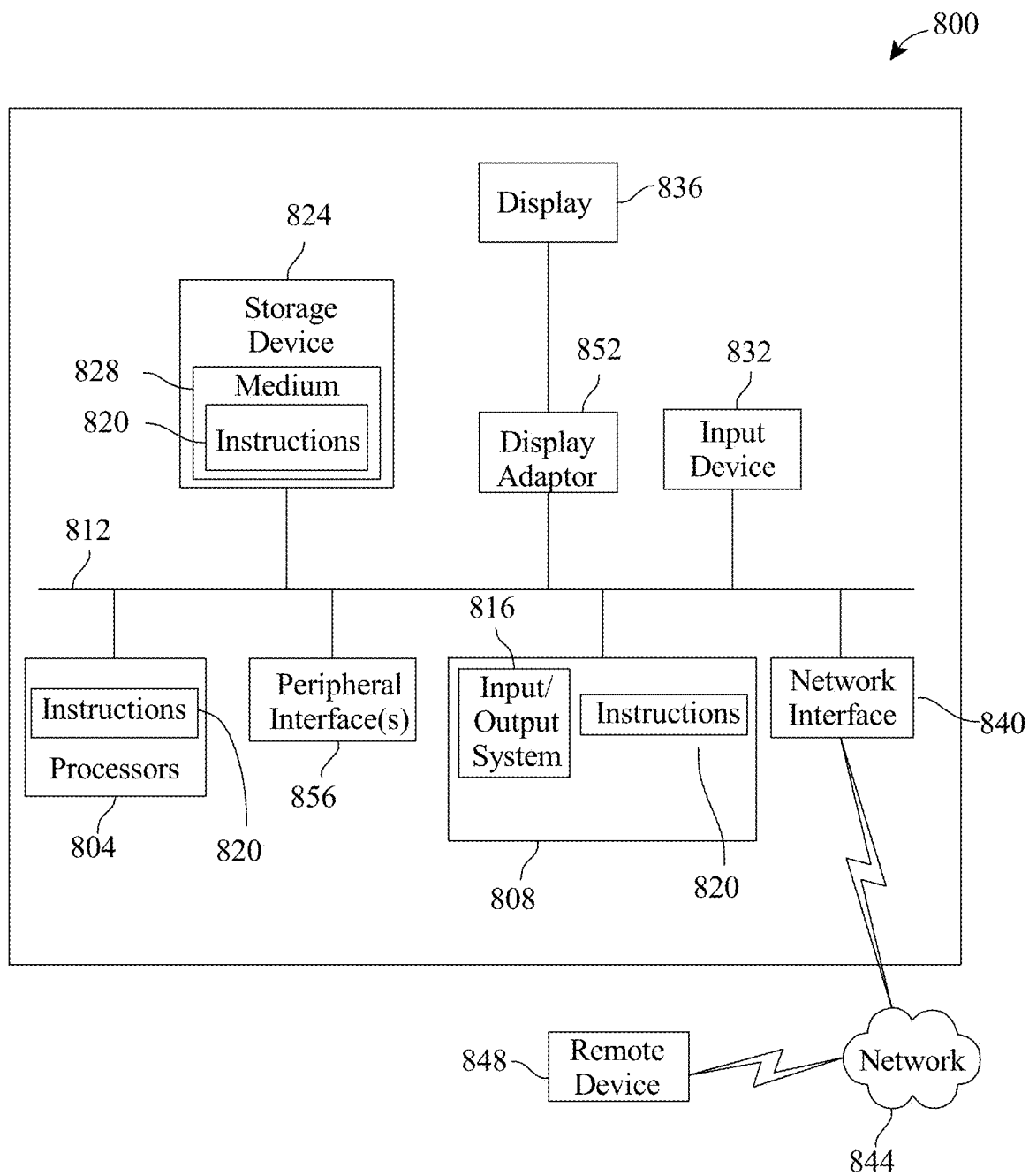
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Memory 808 may include various components (e.g., machine-readable media) including, but not limited to, a random access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of modeling a necrotized tissue volume in an ablation procedure, the method comprising:
   providing, at a radiology workstation, a computer model of a volume of human tissue;
   simulating, by the radiology workstation, an ablation site in the computer model;
   detecting, by the radiology workstation and in the computer model, at least a preferential pathway for heated vapor produced due to ablation of the tissue, wherein the at least a preferential pathway intersects the ablation site;
   determining, by the radiology workstation, a proportion of vapor escaping to the at least a preferential pathway during an ablation procedure;

determining, by the radiology workstation, a heat distribution at the ablation site as a function of the distribution of vapor; and generating, by the radiology workstation, a simulation of a necrotized tissue volume in the volume of human tissue, wherein the simulation of the necrotized tissue volume represents a volume of tissue necrotized by heat during an ablation procedure performed at the ablation site.

2. The method of claim 1, wherein providing the computer model further comprises generating the computer model.

3. The method of claim 2, wherein generating the computer model further comprises generating the computer model from an image of the volume of human tissue.

4. The method of claim 2, wherein generating the computer model further comprises registering a virtual model of an organ over an image of the volume of human tissue.

5. The method of claim 1, wherein simulating the ablation site further comprises simulating a probe insertion.

6. The method of claim 1, wherein detecting the at least a preferential pathway further comprises detecting, in a virtual model of an organ, a pathway that intersects the ablation site.

7. The method of claim 1, wherein detecting the at least a preferential pathway further comprises detecting a probe insertion pathway.

8. The method of claim 1, wherein detecting the at least a preferential pathway further comprises:
introducing an image enhancement substance into the ablation site;
capturing an image of the ablation site with the image enhancement substance; and
detecting the at least a preferential pathway as a function of the image of the ablation site.

9. The method of claim 1, wherein determining the distribution of vapor to the at least a preferential pathway further comprises:
determining a flow rate of vapor into the at least a preferential pathway; and
determining the distribution of vapor to the at least a preferential pathway as a function of the flow rate.

10. The method of claim 9, wherein determining the distribution of vapor as a function of the flow rate further comprises:
determining a rate of vapor generation;
comparing the flow rate to the rate of vapor generation; and
determining the distribution of vapor to the at least a preferential pathway as a function of the comparison.

11. The method of claim 1, wherein determining the distribution of vapor to the at least a preferential pathway further comprises:
deriving a surface area of the at least a preferential pathway; and
determining the distribution of vapor as a function of the surface area.

12. The method of claim 1, wherein determining the distribution of vapor to the at least a preferential pathway further comprises:
deriving a volume of the at least a preferential pathway; and
determining the distribution of vapor as a function of the volume.

13. The method of claim 1, wherein determining the heat distribution at the ablation site further comprises:
identifying a proportion of heat converted to vapor; and
determining the heat distribution at the ablation site as a function of the proportion of the heat converted to vapor and the distribution of vapor to the at least a preferential pathway.

14. The method of claim 13 further comprising calculating a distribution of heat transferred to the tissue by the vapor.

15. The method of claim 1, wherein generating the simulation of the necrotized tissue volume further comprises simulating a primary ablation volume as a function of heat present at the ablation site.

16. The method of claim 1, wherein generating the simulation of the necrotized tissue volume further comprises simulating necrotized tissue along the at least a preferential pathway.

17. The method of claim 1 further comprising comparing a simulated volume to a volume of tissue intended to be necrotized.

18. A system for modeling a necrotized tissue volume in an ablation procedure, the system comprising:
an radiology workstation, wherein the radiology workstation is designed and configured to provide a computer model of a volume of human tissue based on corporeal image data, simulate an ablation site in the computer model, detect, in the computer model, at least a preferential pathway for heated vapor produced due to ablation of the tissue, wherein the at least a preferential pathway intersects the ablation site, determine a proportion of vapor escaping to the at least a preferential pathway during an ablation procedure, determiner a heat distribution at the ablation site as a function of the distribution of vapor, and generate a simulation of a necrotized tissue volume in the volume of human tissue, wherein the simulation of the necrotized tissue volume represents a volume of tissue necrotized by heat during an ablation procedure performed at the ablation site.

19. The system of claim 14 further comprising a radiological machine in communication with the radiology workstation.

20. The system of claim 14 further comprising an image-guided surgical suite in communication with the radiology workstation.

* * * * *